United States Patent
Matsuda et al.

(10) Patent No.: US 8,759,072 B2
(45) Date of Patent: Jun. 24, 2014

(54) PROTEIN EXHIBITING ACTIVITY OF PYRETHRIN BIOSYNTHETIC ENZYME, GENE ENCODING THE PROTEIN, AND VECTOR BEARING THE GENE

(75) Inventors: Kazuhiko Matsuda, Nara (JP); Yukio Kikuta, Toyonaka (JP)

(73) Assignees: An Educational Foundation Kinki University, Osaka (JP); Dainihon Jochugiku Co., Ltd., Osaka (JP)

( * ) Notice: Subject to any disclaimer, the term of this patent is extended or adjusted under 35 U.S.C. 154(b) by 186 days.

(21) Appl. No.: 13/137,327

(22) Filed: Aug. 5, 2011

(65) Prior Publication Data

US 2012/0040434 A1 Feb. 16, 2012

Related U.S. Application Data

(63) Continuation-in-part of application No. 12/457,193, filed on Jun. 3, 2009, now Pat. No. 8,129,180.

(30) Foreign Application Priority Data

Aug. 13, 2008 (JP) ................................ 2008-208295

(51) Int. Cl.
C12N 15/54 (2006.01)
C12N 9/10 (2006.01)

(52) U.S. Cl.
USPC ..................... 435/252.3; 435/320.1; 435/193; 435/419; 435/325; 536/23.2

(58) Field of Classification Search
None
See application file for complete search history.

(56) References Cited

U.S. PATENT DOCUMENTS

| 8,124,074 B2 | 2/2012 | Foster et al. |
| 2010/0062510 A1 | 3/2010 | Matsuda et al. |

FOREIGN PATENT DOCUMENTS

| EP | 0 124 049 A2 | 11/1984 |
| JP | A-9-504684 | 5/1997 |
| WO | WO 95/00634 A1 | 1/1995 |

OTHER PUBLICATIONS

Y. Kikuta et al. Identification and characterization of a GDSL lipase-like protein that catalyzes the ester-forming reaction for pyrethrin biosynthesis in *Tanacetum cinerariifolium*—A new target for plant protection, The Plant Journal 71:183-193 (2012).*
R. Kalscheuer and A. Steinbuchel, A Novel Bifunctional Wax Ester Synthase/Acyl-CoA: Diacylglycerol Acyltransferase Mediates Wax Ester and Triacylglycerol Biosynthesis in *Acihetobacter calcoaceticus* ADP1. J. Biol. Chem. 278:8075-8082 (2003).
J. Luo et al., Convergent evolution in the BAHD family of acyl transferases: identification and characterization of anthocyanin acyl transferases from *Arabidopsis thaliana*. Plant J. 50:678-695 (2007).
M. Takahashi et al., "Research regarding pyrethrin biosynthesis in pyrethrum flowers: Acyl-CoA transferase contributing Ester bonding." Collection in summarized lecture in agricultural chemical society of Japan ABSJ in 2006.
Rivera et al., "Chrysanthemyl Diphosphate Synthase: Isolation of the Gene and Characterization of the Recombinant Non-Head-to-Tail Monoterpene Synthase from *Chrysanthemum cinerariaefolium*," PNAS, vol. 98, No. 8, pp. 4373-4378, Apr. 10, 2001.
"Natural Pyrethrins," Mass Meeting of Agricultural Chemical Scientific Society, Mar. 5, 2004.
Matsuda et al., "Biosynthesis of Pyrethrin I in Seedlings of *Chrysanthemum cinerariaefolium*," Phytochemistry, vol. 66, pp. 1529-1535, 2005.
Hitmi et al., "The Production of Pyrethrins by Plant Cell and Tissue Cultures of *Chrysanthemum cinerariaefolium* and *Tagetes Species*," Critical Reviews in Biochemistry and Molecular Biology, vol. 35, No. 5, pp. 317-337, 2000.
Crombie, "Chemistry and Biosynthesis of Natural Pyrethrin," Pestic. Sci., vol. 11, pp. 102-118, 1980.
GenBank Accession No. JN418894.1, Feb. 2012, www.ncbi.nlm.nih.gov.
"Cloning Vector pMAL-c4E," complete sequence, Oct. 22, 2007, www.neb.com/tools-and-resources/interactive-tools/dna-sequences-and-maps-tool.
"pMAL™ Protein Fusion and Purification System,", New England BioLabs, Version 5.3, pp. 1-52, 2006.
GenBank Accession No. JN418990.1, Feb. 2012, www.ncbi.nlm.nih.gov.
Jul. 31, 2013 Office Action issued in U.S. Appl. No. 13/720,574.

* cited by examiner

*Primary Examiner* — Rebecca Prouty
(74) *Attorney, Agent, or Firm* — Oliff PLC

(57) ABSTRACT

The present invention relates to an enzyme determining amino acid sequences of an enzyme involved in pyrethrin biosynthesis and a base sequence of the gene thereof; constructing vectors bearing the gene and transformants; and extractable from plant bodies producing pyrethrin by applying such creative techniques to plant bodies with faster growth aiming to provide a method to efficiently produce pyrethrin; and the enzyme is a gene encoding a protein of the following (i) or (ii) or (iii):

(i) a protein consisting of an amino acid sequence shown in Sequence No. 1; or
(ii) a protein consisting of an amino acid sequence shown in Sequence No. 5, or a protein consisting of an amino acid sequence shown in Sequence No. 6, or a protein consisting of an amino acid sequence shown in Sequence No. 7, or a protein consisting of an amino acid sequence shown in Sequence No. 8,
(iii) a protein consisting of an amino acid sequence including one or more of a substitution, deletion, insertion, and/or addition of amino acid in the amino acid sequence shown in Sequence No. 1, in which the protein exhibits activity of pyrethrin biosynthetic enzyme.

5 Claims, 8 Drawing Sheets

FIG 1

(e) Sequence No.5

MAVASRKLGALVLVAVLCLSLPTGCLSSQQAAALFIFGDSVFDPGNNNHINTHVNFKANFWPYGQS
YFSSPTGRFSDGRIIPDFIAEYASLPIIPAYLEPNNDFTHGANFASAGAGALIASHAGLAVGLQTQLRY
FGDLVDHYRQNLGDIKSRQLLSDAVYLFSCGGNDYQSPYYPYTQEQYVDIVIGNMTNVIKGIYEKGG
RKFGVVNVPLIGCWPGMRAKQPGNACNTEVDELTRLHNQAFAKRLEHLEKELEGFVYAKFDLSTAIL
NRMKNPSKYGFKEGESACCGSGPFGGNYDCGRIKEFGLCDNATEYFFFDPFHPNELASRQFAEMF
WDGDSMVTQPYNLKALFEGKPSTKFLPNDEL (f) Sequence No.6

MAVASRKLGALVLVAVLCLSLPTGCLSSQQAAALFIFGDSVFDPGNNNHINTHVNFKANFWPYGQS
YFSSPTGRFSDGRIIPDFIAEYASLPIIPAYLEPNNDFTHGANFASAGAGALIASHAGLAVGLQTQLRY
FGDLVDHYRQNLGDIKSRQLLSDAVYLFSCGGNDYQSPYYPYTQEQYVDIVIGNMTNVIKGIYEKGG
RKFGVVNVPLIGCWPGMRAKQPGNTCNTEVDELTRLHNQAFAKRLEQLEKQLEGFVYAKFDLSTAI
LNRMKNPSKYGFKEGESACCGSGPFGGNYDCGRIKEFGLCDNATEYFFFDPFHPNELASRQFAEMF
WDGDSMVTQPYNLKALFEGKPSTKFLPNDEL (g) Sequence No.7

MAVASRKLGALVLVAVLCLSLPTGCLSSQQAAALFIFGDSVFDPGNNNHINTHVNFKANFWPYGQS
YFSSPTGRFSDGRIIPDFIAEYASLPIIPAYLEPNNDFTHGANFASAGAGALIASHAGLAVGLQTQLRY
FGDLVDHYRQNLGDIKSRQLLSDAVYLFSCGGNDYQSPYYPYTQEQYVDIVIGNMTNVIKGIYEKGG
RKFGVVNVPLIGCWPGMRAKQPGNTCNTEVDELTRLHNQAFAKRLEQLEKQLEGFVYAKFDLSTAI
LNRMKNPSKYGFKEGESACCGSGPFGGNYDCGRIKEFGLCDNATEYFFFDPFHPNELASRQFAEMF
WDGDSMVTQPYNLKALFEGKPSTKYLPNDEL (h) Sequence No.8

MAVASRKLGALVLVAVLCLSLPTGCLSSQQAAALFIFGDSVFDPGNNNHINTHVNFKANFWPYGQS
YFSSPTGRFSDGRIIPDFIAEYASLPIIPAYLEPNNYFTHGANFASAGAGALIASHAGLAVGLQTQLRY
FGDLVDHYRQNLGDIKSRQLLSDAVYLFSCGGNDYQSPYYPYTQEQYVDIVIGNMTNVIKGIYEKGG
RKFGVVNVPLIGCWPGMRAKQPGNTCNTEVDELTRLHNQAFAKRLEQLEKQLEGFVYAKFDLSTAI
LNRMKNPSKYGFKEGESACCGSGPFGGNYDCGRIKEFGLCDNATEYFFFDPFHPNELASRQFAEMF
WDGDSMVTQPYNLKALFEGKPSTKYLPNDEL

FIG. 2A (a) Sequence No.9

ATGGCTGTTG CAAGCAGCAA WCGGGGTGCT CTTGTTTTGG TTGCTGTTTT GTGTCTTTCA
CTACCTACAG GTTGCCTGAG TTCTCAACAA GCTGCTGCAC TATTTATATT TGGTGATTCG
GTTTTCGATC CTGGTAACAA TAACCACATC AACACCCATG TTAATTTTAA AGCGAACTTT
TGGCCATATG GTCAATCCTA CTTCAGTTCA CCAACTGGTA GATTCTCTGA TGGCCGTATC
ATCCCTGATT TCATTGCTGA GTATGCAAGT CTGCCTATCA TTCCTGCGTA TCTCGAGCCA
AACAATGATT TTACGCATGG AGCMAACTTT GCGTCAGCAG GAGCCGGTGC CTTGATTGCC
TCCCATGCTG GACTTGCAGT TGGCCTTCAA ACACAACTAC ATTACTTTGG CGATTTAGTA
GACCATTATC GGCAGAATTT AGGTGATATT AAATCTAGGC AGCTACTATC CGATGCTGTC
TACTTGTTTA GCTGTGGAGG TAACGACTAC CAAAGCCCTT ACTATCCATA TACTCAAGAG
CAATACGTGG ACATTGTGAT TGGAAACATG ACTAACGTCA TCAAGGGAAT ATACGAAAAA
GGTGGAAGAA AATTTGGGGT TGTGAATGTC CCGCTTATAG GCTGTTGGCC GGGAATGCGA
GCAAAACAAC CTGGAAATGC TTGCAACACA GAGGTCGATG AACTTACTAG ACTACACAAT
CAAGCATTTG CAAAAACACT AGAACATTTG GAGAAACAGT TGGAAGGCTT TGTGTATGCT
AAATTCGATC TTTCAACTGC CATTCTCAAT AGAATGAAGA ACCCCTCAAA ATATGGTTTT
AAGGAAGGCG AGAGCGCATG TTGCGGTAGT GGTCCTTTTG GAGGGAATTA TGATTGTGGC
AGAATAAAAG AGTTTGGACT ATGTGATAAT GCAACTGAGT ATTTTTTCTT TGACCCTTTT
CATCCTAATG AATTGGCGAG TCGCCAATTT GCAGAGATGT TTTGGGATGG GGATTCCATG
GTCACACAGC CTTACAATTT GAAAGCACTC TTTGAAGGGA AGCCATCAAC AAAATATCTC
CCAAATGATG AGCTCTAA (b) Sequence No.10

ATGGCTGTTG CAAGCAGAAA ACTGGGTGCT CTTGTTTTGG TTGCTGTTTT GTGTCTTTCA
CTACCTACAG GTTGCCTTAG TTCTCAACAA GCTGCTGCAC TATTTATATT TGGTGATTCG
GTTTTCGATC CTGGTAACAA TAACCACATC AACACCCATG TTAATTTTAA AGCGAACTTT
TGGCCATATG GTCAATCCTA CTTCAGTTCA CCAACTGGTA GATTCTCTGA TGGCCGTATC
ATCCCTGATT TCATTGCTGA GTATGCAAGT CTGCCTATCA TTCCTGCGTA TCTCGAGCCA
AACAATGATT TTACGCATGG AGCMAACTTT GCGTCAGCAG GAGCTGGTGC CTTGATTGCC
TCCCATGCTG GACTTGCAGT TGGCCTTCAA ACACAACTAC GTTACTTTGG CGATTTAGTA
GACCATTATC GGCAGAATTT AGGTGATATT AAATCTAGGC AGCTACTATC CGATGCTGTC
TACTTGTTTA GCTGTGGAGG TAACGACTAC CAAAGCCCTT ACTATCCATA TACTCAAGAG
CAATACGTCG ACATTGTGAT TGGAAACATG ACTAACGTCA TCAARGGAAT ATACGAAAAA
GGTGGAAGAA AATTTGGGGT TGTGAATGTC CCGCTTATAG GCTGTTGGCC GGGAATGCGA
GCAAAACAAC CTGGAAATGC TTGCAACACA GAGGTCGATG AACTTACTAG ACTACACAAT
CAAGCATTTG CAAAAAGACT AGAACATTTG GAGAAAGAGT TGGAAGGCTT TGTGTATGCT
AAATTCGATC TTTCAACTGC CATTCTCAAT AGAATGAAGA ACCCCTCAAA ATATGGTTTT
AAGGAAGGCG AGAGCGCATG TTGCGGTAGT GGTCCTTTTG GAGGGAATTA TGATTGTGGC
AGAATAAAAG AGTTTGGACT ATGTGATAAT GCAACTGAGT ATTTTTTCTT TGACCCTTTT
CATCCTAATG AATTGGCGAG TCGCCAATTT GCAGAGATGT TTTGGGATGG GGATTCCATG
GTCACACAGC CTTACAATTT GAAAGCACTC TTTGAAGGGA AGCCATCAAC AAAATTTCTC
CCAAATGATG AGCTCTAA

FIG. 2B (c) Sequence No.11

ATGGCTGTTG CAAGCAGAAA ACTGGGTGCT CTTGTTTTGG TTGCTGTTTT GTGTCTTTCA
CTACCTACAG GTTGCCTTAG TTCTCAACAA GCTGCTGCAC TATTTATATT TGGTGATTCG
GTTTTCGATC CTGGTAACAA TAACCACATC AACACCCATG TTAATTTTAA AGCGAACTTT
TGGCCATATG GTCAATCCTA CTTCAGTTCA CCAACTGGTA GATTCTCTGA TGGCCGTATC
ATCCCTGATT TCATTGCTGA GTATGCAAGT CTGCCTATCA TTCCTGCGTA TCTCGAGCCA
AACAATGATT TTACGCATGG AGCCAACTTT GCGTCAGCAG GAGCTGGTGC CTTGATTGCC
TCCCATGCTG GACTTGCAGT TGGCCTTCAA ACACAACTAC GTTACTTTGG CGATTTAGTA
GACCATTATC GGCAGAATTT AGGTGATATT AAATCTAGGC AGCTACTATC CGATGCTGTC
TACTTGTTTA GCTGTGGAGG TAACGACTAC CAAAGCCCTT ACTATCCATA TACTCAAGAG
CAATACGTGG ACATTGTGAT TGGAAACATG ACTAACGTCA TCAAGGGAAT ATACGAAAAA
GGTGGAAGAA AATTTGGTGT TGTGAATGTC CCGCTTATAG GCTGTTGGCC GGGAATGCGA
GCAAAACAAC CTGGAAATAC TTGCAACACA GAGGTCGATG AACTTACTAG ACTACACAAT
CAAGCATTTG CAAAAAGACT AGAACAATTG GAGAAACAGT TGGAAGGCTT TGTGTATGCT
AAATTCGATC TTTCAACTGC CATTCTCAAT AGAATGAAGA ACCCCTCAAA ATATGGTTTT
AAGGAAGGCG AGAGCGCATG TTGCGGTAGT GGTCCTTTTG GAGGGAATTA TGATTGTGGC
AGAATAAAAG AGTTTGGACT ATGTGATAAT GCAACTGAGT ATTTTTTCTT TGACCCTTTT
CATCCTAATG AATTGGCGAG TCGCCAATTT GCAGAGATGT TTTGGGATGG GGATTCCATG
GTCACACAGC CTTACAATTT GAAAGCACTC TTTGAAGGGA AGCCATCAAC AAAATTTCTC
CCAAATGATG AGCTCTAA (d) Sequence NO.12

ATGGCTGTTG CAAGCAGAAA ACTGGGTGCT CTTGTTTTGG TTGCTGTTTT GTGTCTTTCA
CTACCTACAG GTTGCCTTAG TTCTCAACAA GCTGCTGCAC TATTTATATT TGGTGATTCG
GTTTTCGATC CTGGTAACAA TAACCACATC AACACCCATG TTAATTTTAA AGCGAACTTT
TGGCCATATG GTCAATCCTA CTTCAGTTCA CCAACTGGTA GATTCTCTGA TGGCCGTATC
ATCCCTGATT TCATTGCTGA GTATGCAAGT CTGCCTATCA TTCCTGCGTA TCTCGAGCCA
AACAATGATT TTACGCATGG AGCMAACTTT GCGTCAGCAG GAGCTGGTGC CTTGATTGCC
TCCCATGCTG GACTTGCAGT TGGCCTTCAA ACACAACTAC GTTACTTTGG CGATTTAGTA
GACCATTATC GGCAGAATTT AGGTGATATT AAATCTAGGC AGCTACTATC CGATGCTGTC
TACTTGTTTA GCTGTGGAGG TAACGACTAC CAAAGCCCTT ACTATCCATA TACTCAAGAG
CAATACGTSG ACATTGTGAT TGGAAACATG ACTAACGTCA TCAAGGGAAT ATACGAAAAA
GGTGGAAGAA AATTTGGTGT TGTGAATGTC CCGCTTATAG GCTGTTGGCC GGGAATGCGA
GCAAAACAAC CTGGAAATAC TTGCAACACA GAGGTCGATG AACTTACTAG ACTACACAAT
CAAGCATTTG CAAAAAGACT AGAACAATTG GAGAAACAGT TGGAAGGCTT TGTGTATGCT
AAATTCGATC TTTCAACTGC CATTCTCAAT AGAATGAAGA ACCCCTCAAA ATATGGTTTT
AAGGAAGGCG AGAGCGCATG TTGCGGTAGT GGTCCTTTTG GAGGGAATTA TGATTGTGGC
AGAATAAAAG AGTTTGGACT ATGTGATAAT GCAACTGAGT ATTTTTTCTT TGACCCTTTT
CATCCTAATG AATTGGCGAG TCGCCAATTT GCAGAGATGT TTTGGGATGG GGATTCCATG
GTCACACAGC CTTACAATTT GAAAGCACTC TTTGAAGGGA AGCCATCAAC AAAATATCTC
CCAAATGATG AGCTCTAA

FIG. 2C (e) Sequence No.13

ATGGCTGTTG CAAGCAGAAA ACTGGGTGCT CTTGTTTTGG TTGCTGTTTT GTGTCTTTCA
CTACCTACAG GTTGCCTTAG TTCTCAACAA GCTGCTGCAC TATTTATATT TGGTGATTCG
GTTTTCGATC CTGGTAACAA TAACCACATC AACACCCATG TTAATTTTAA AGCGAACTTT
TGGCCATATG GTCAATCCTA CTTCAGTTCA CCAACTGGTA GATTCTCTGA TGGCCGTATC
ATCCCTGATT TCATTGCTGA GTATGCAAGT CTGCCTATCA TTCCTGCGTA TCTCGAGCCA
AACAATTATT TTACGCATGG AGCCAACTTT GCGTCAGCAG GAGCTGGTGC CTTGATTGCC
TCCCATGCTG GACTTGCAGT TGGCCTTCAA ACACAACTAC GTTACTTTGG CGATTTAGTA
GACCATTATC GGCAGAATTT AGGTGATATT AAATCTAGGC AGCTACTATC CGATGCTGTC
TACTTGTTTA GCTGTGGAGG TAACGACTAC CAAAGCCCTT ACTATCCATA TACTCAAGAG
CAATACGTGG ACATTGTGAT TGGAAACATG ACTAACGTCA TCAAGGGAAT ATACGAAAAA
GGTGGAAGAA AATTTGGTGT TGTGAATGTC CCGCTTATAG GCTGTTGGCC GGGAATGCGA
GCAAAACAAC CTGGAAATAC TTGCAACACA GAGGTCGATG AACTTACTAG ACTACACAAT
CAAGCATTTG CAAAAAGACT AGAACAATTG GAGAAACAGT TGGAAGGCTT TGTGTATGCT
AAATTCGATC TTTCAACTGC CATTCTCAAT AGAATGAAGA ACCCCTCAAA ATATGGTTTT
AAGGAAGGCG AGAGCGCATG TTGCGGTAGT GGTCCTTTTG GAGGGAATTA TGATTGTGGC
AGAATAAAAG AGTTTGGACT ATGTGATAAT GCAACTGAGT ATTTTTTCTT TGACCCTTTT
CATCCTAATG AATTGGCGAG TCGCCAATTT GCAGAGATGT TTTGGGATGG GGATTCCATG
GTCACACAGC CTTACAATTT GAAAGCACTC TTTGAAGGGA AGCCATCAAC AAAATATCTC
CCAAATGATG AGCTCTAA

Fig 3

[Structure of pyrethrins]

|  | Side chain of chrysanthemic acid moiety (R1) | Side chain of rethrolone moiety (R2) |
|---|---|---|
| Pyrethrin I | -CH3 | -CH=CH2 |
| Pyrethrin II | -COOCH3 | -CH=CH2 |
| Cinerin I | -CH3 | -CH3 |
| Cinerin II | -COOCH3 | -CH3 |
| Jasmolin I | -CH3 | -CH2CH3 |
| Jasmolin II | -COOCH3 | -CH2CH3 |

Chrysanthemic acid moiety   Rethrolone moiety

Fig. 4

[Biosynthesis reaction of ester by acyltransferase]

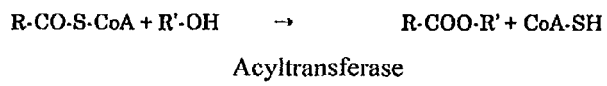

Acyltransferase

Fig. 5

[Biosynthesis reaction of pyrethrin]

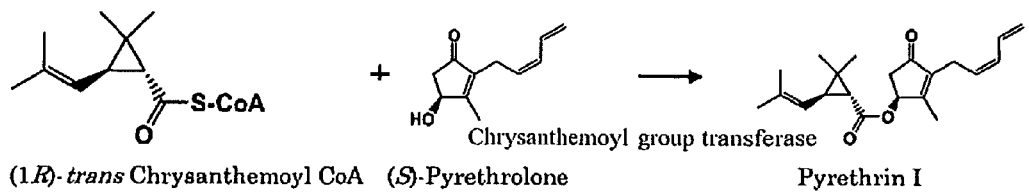

(1R)-trans Chrysanthemoyl CoA   (S)-Pyrethrolone   Chrysanthemoyl group transferase   Pyrethrin I Fig.6
[Examples of HPLC analysis results of pyrethrin-biosynthesis reaction solution]
(a) Fraction without enzyme activity    (b) Fraction with enzyme activity
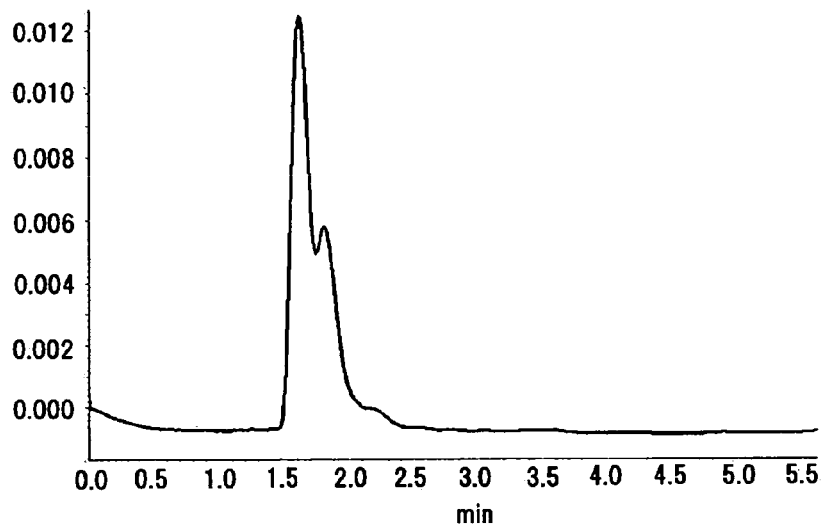
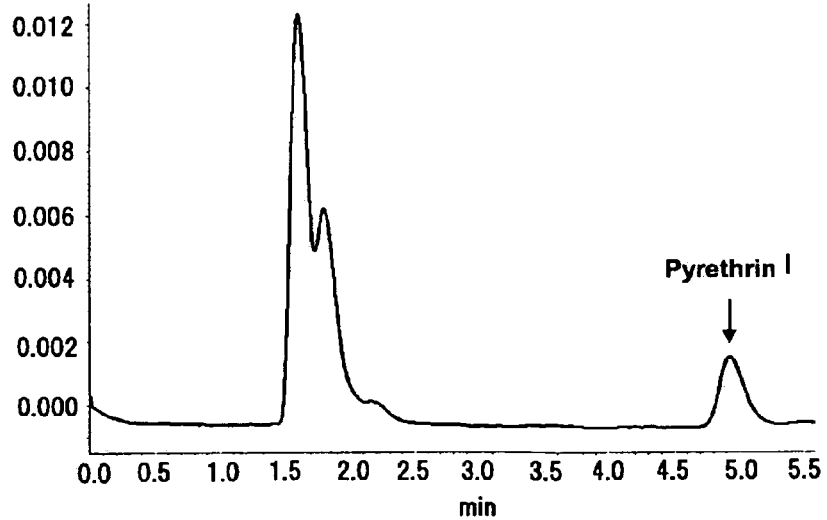

Fig.7

[Flow of enzyme purification from plant bodies]

Preparation of crude enzyme solution
↓
Fractionation by ammonium sulfate precipitation
↓
Crude purification by batch method using Phenyl Sepharose
↓
Anion Exchange Chromathography (Q Sepharose)
↓
Hydrophobic Chromathography (Phenyl Superose)
↓
Gel Filtration (Superdex 75)

Fig. 8

Electrophoresis (SDS-PAGE) photo image of purified pyrethrin biosynthetic enzyme

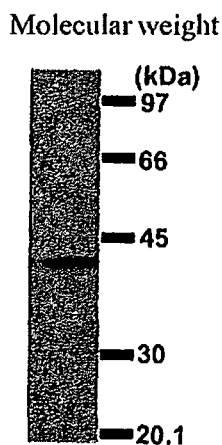

Fig. 9

(a) : Amino acid Sequence No. 14
SQQAAALFIFGDSVFDPGNNNHINTHVNFKANF (b) : Amino acid Sequence No. 15
QNLGDIK (c) : Amino acid Sequence No. 16
QLEGFVYAK

PROTEIN EXHIBITING ACTIVITY OF PYRETHRIN BIOSYNTHETIC ENZYME, GENE ENCODING THE PROTEIN, AND VECTOR BEARING THE GENE This is a continuation-in-part of application Ser. No. 12/457,193 filed Jun. 3, 2009, now U.S. Pat. No. 8,129,180, and claims the benefit of Japanese Application No. 2008-208295 filed Aug. 13, 2008. The entire disclosure of the prior applications are hereby incorporated by reference in their entirety.

TECHNICAL FIELD

The present invention relates to a protein exhibiting activity of a pyrethrin biosynthetic enzyme, a gene encoding thereof, and vector bearing the gene.

BACKGROUND ART

Pyrethrin which is a secondary metabolite contained in pyrethrum exhibits excellent insecticidal activity against insects as well as being an ideal feature as an insecticidal constituent where toxicity against mammals is low, and is widely used for mosquito coils, and insecticide sprays and powders. Recently, demand for pyrethrin has decreased because of the remarkable development of synthetic pyrethroid. However, pyrethrin still has a high utility value as a plant-derived, and environmentally friendly material for insecticides, and further investigation has continued to a point where pyrethrin can be obtained inexpensively and effectively. In particular, the existence value of the above pyrethrin, a secondary metabolite, has been emphasized again, because of increasing oil prices, which is a raw material of synthetic pyrethroid, and the like.

Pyrethrin is mainly extracted from the flower part of pyrethrum. However, the growth duration of pyrethrum until flowering is very long, over three years. It is considered that selection and breeding of high-producing strains of pyrethrum and promotion of pyrethrin biosynthesis in plant cells of the same or different species have a beneficial effect as a means for increasing the efficiency of pyrethrin production.

Pyrethrin has an ester-bonded structure between chrysanthemic acid that is a monoterpene carboxylic acid and rethrolones (alcohols), which is a metabolite of fatty acid oxidation (FIG. 3). It is known that in biosynthesis of pyrethrin, chrysanthemic acid and rethrolones are biosynthesized in different metabolic pathways and an ester binding is eventually formed therebetween.

Methods for increasing efficiency of the above-described biosynthesis of pyrethrin include use of genes involved in the biosynthesis. In order to implement biosynthesis of pyrethrin, isolation and identification of the relevant gene is crucial.

Meanwhile, various ester compounds produced by plant cells are biosynthesized by catalysis of acyltransferase from CoA thioester of carboxylic acid (acyl-CoA, RCO-S-CoA) and alcohol (R'—OH) as substrates (FIG. 4), and these biosyntheses are described, for example, in Non-Patent Document 1 and 2.

As an example of such acyltransferase in the pyrethrin biosynthesis, existence of chrysanthemoyl/pyrethroyl transferase (pyrethrin biosynthetic enzyme) which uses (1R)-trans-chrysanthemoyl-CoA and (S)-pyrethrolone as substrates have been predicted, however, there has been no isolated and specific composition based on an amino acid sequence, and naturally a gene encoding the protein based on such an amino acid sequence is not particularly sought.

Meanwhile, Japanese Patent Application Publication No. H9-504684 discloses an amino acid sequence of chrysanthemyl diphosphate synthase, an enzyme that can catalyze synthesis of chrysanthemyl diphosphate, which is adopted as a raw material for chemical synthesis of pyrethrin, and a sequence of a gene coding a protein based on such an amino acid sequence. However, there has been neither disclosure nor suggestion about the gene encoding the enzyme per se, which can catalyze the above pyrethrin biosynthesis, and the gene coding protein based on such an amino acid sequence. As obvious from the situation in the conventional art, elucidation of the gene encoding the above enzyme protein through identification of the enzyme involved in the pyrethrin biosynthesis, and effective biosynthesis of pyrethrin based on knowledge of genetic engineering have not been achieved.

[Patent Document 1] Japanese patent application publication No. H9-504684

[Non-Patent Document 1] R. Kalscheuer and A. Steinbuchel, A novel bifunctional wax ester synthase/acyl-CoA: diacylglycerol acyltransferase mediates wax ester and triacylglycerol biosynthesis in *Acinetobacter calcoaceticus* ADP1. J. Biol. Chem. 278:8075-8082 (2003)

[Non-Patent Document 2] J. Luo et al., Convergent evolution in the BAHD family of acyl transferases: identification and characterization of anthocyanin acyl transferases from *Arabidopsis thaliana*. Plant J. 50:678-695 (2007)

DISCLOSURE OF INVENTION, AND PROBLEMS TO BE SOLVED BY THE INVENTION

The present invention aims to determine amino acid sequences of the enzyme involved in pyrethrin biosynthesis and a base sequence of the gene thereof, and to construct vectors bearing the gene and transformants, as well as to provide methods for effectively producing pyrethrin by applying such creative techniques to plants with faster growth.

In order to solve the above issues, inventors of the present invention purified a pyrethrin synthesis enzyme protein by using the pyrethrum flower as a raw material and pyrethrin I synthesis activity as an indicator, and by performing crude fractionation of a protein and crude purification by batch method using hydrophobic resin, and then purification with a predetermined combination of chromatography; and finally analyzed an internal amino acid sequence and amino terminal sequence of the relevant protein as is described below. RACE-PCR was performed and a polynucleotide fragment of an unknown part of the sequence was amplified using a cDNA library obtained from a flower part of pyrethrum as temperate and degenerate primers designed based on crude amino acid sequences, which have been clarified through the above analysis.

An amplified polynucleotide fragment of the base sequence was analyzed with a DNA sequencer. As a result, a gene of coding sequence of a pyrethrin biosynthetic enzyme (herein after "coding sequence" should be designate to be "CDS"), consisting of a bese sequence shown in FIG. 2(*a*), i.e., sequence No 9, and an amino acid sequence encoded by the gene, a sequence shown in FIG. 1 (*a*), i.e., Sequence No. 1(*a*), were determined. The present invention was completed based on such determination of the sequences.

The present invention adopts the following constitution:

What is claimed:

(1) A pyrethrin biosynthetic enzyme, in which raw material of the enzyme is a crude enzyme solution prepared from a pyrethrum flower;

wherein (1R)-trans-chrysanthemoyl-CoA and (S)-pyrethrolone are used as substrates for a test to confirm an active function of the pyrethrum biosynthetic enzyme;
wherein the pyrethrum biosynthetic enzyme is produced by a purification procedure including the sequential steps of:
  obtaining precipitate of crude protein fractionation with ammonium sulfate precipitation;
  crudely purifying the precipitate by batch method using hydrophobic resin;
  purifying the enzyme solution obtained by crude purification, with anion-exchange chromatography;
  purifying with hydrophobic chromatography; and
  purifying with gel filtration,
and wherein produced enzyme is a protein with a molecular weight of approximately 40,000.

(2) A protein of the following (i) or (ii) or (iii), corresponding to an enzyme extractable from plant bodies of producing pyrethrin:
  (i) a protein consisting of an amino acid sequence shown in Sequence No. 1; or
  (ii) a protein consisting of an amino acid sequence shown in Sequence No. 5, or a protein consisting of an amino acid sequence shown in Sequence No. 6, or a protein consisting of an amino acid sequence shown in Sequence No. 7, or a protein consisting of an amino acid sequence shown in Sequence No. 8, wherein an amino acid of order number 6, 8, 103, 134, 227, 246, 249, 253, 359 in amino acid sequence No. 1 is substituted according to following list or

| Designation of sequence of amino acid | Order number of amino acid sequence | | | | | | | | |
|---|---|---|---|---|---|---|---|---|---|
| | 6 | 8 | 103 | 134 | 227 | 246 | 249 | 253 | 359 |
| Amino acid sequence No. 1 | Ser | Arg | Asp | His | Ala | Thr | His | Gln | Tyr |
| Amino acid sequence No. 5 | Arg | Leu | Asp | Arg | Ala | Arg | His | Glu | Phe |
| Amino acid sequence No. 6 | Arg | Leu | Asp | Arg | Thr | Arg | Gln | Gln | Phe |
| Amino acid sequence No. 7 | Arg | Leu | Asp | Arg | Thr | Arg | Gln | Gln | Tyr |
| Amino acid sequence No. 8 | Arg | Leu | Tyr | Arg | Thr | Arg | Gln | Gln | Tyr |

(iii) a protein consisting of an amino acid sequence including one or more of a substitution, deletion, insertion, and/or addition of an amino acid in the amino acid sequence shown in Sequence No. 1, in which the protein exhibits activity of a pyrethrin biosynthetic enzyme.

(3) A protein consisting of an amino acid sequence shown in Sequence No. 2, or a protein consisting of an amino acid sequence shown in Sequence No. 3, or a protein consisting of an amino acid sequence shown in Sequence No. 4, corresponding to an enzyme extractable from plant bodies producing pyrethrin.

(4) A gene encoding a protein of the following (i) or (ii) or (iii), corresponding to an enzyme extractable from plant bodies producing pyrethrin:
  (i) a protein consisting of an amino acid sequence shown in Sequence No. 1; or
  (ii) a protein consisting of an amino acid sequence shown in Sequence No. 5, or a protein consisting of an amino acid sequence shown in Sequence No. 6, or a protein consisting of an amino acid sequence shown in Sequence No. 7, or a protein consisting of an amino acid sequence shown in Sequence No. 8, wherein an amino acid of order number 6, 8, 103, 134, 227, 246, 249, 253, 359 in amino acid sequence No. 1 is substituted according to following list or

| Designation of sequence of amino acid | Order number of amino acid sequence | | | | | | | | |
|---|---|---|---|---|---|---|---|---|---|
| | 6 | 8 | 103 | 134 | 227 | 246 | 249 | 253 | 359 |
| Amino acid sequence No. 1 | Ser | Arg | Asp | His | Ala | Thr | His | Gln | Tyr |
| Amino acid sequence No. 5 | Arg | Leu | Asp | Arg | Ala | Arg | His | Glu | Phe |
| Amino acid sequence No. 6 | Arg | Leu | Asp | Arg | Thr | Arg | Gln | Gln | Phe |
| Amino acid sequence No. 7 | Arg | Leu | Asp | Arg | Thr | Arg | Gln | Gln | Tyr |
| Amino acid sequence No. 8 | Arg | Leu | Tyr | Arg | Thr | Arg | Gln | Gln | Tyr |

(iii) a protein consisting of an amino acid sequence including one or more of a substitution, deletion, insertion, and/or addition of an amino acid in the amino acid sequence shown in Sequence No. 1, in which the protein exhibits activity of a pyrethrin biosynthetic enzyme, (5). A gene according to (4), consisting of a base sequence shown in Sequence No. 9, or Sequence No. 10, or Sequence No. 11, or Sequence No. 12, or Sequence No. 13; wherein the gene encodes the protein of (i) or (ii).

(6). A gene encoding any of the following proteins: a protein consisting of an amino acid sequence shown in Sequence No. 2, or a protein consisting of an amino acid sequence shown in Sequence No. 3, or a protein consisting of an amino acid sequence shown in Sequence No. 4, corresponding to an enzyme extractable from plant bodies producing pyrethrin.

(7). A vector bearing a gene according to (4).
(8). A vector bearing a gene according to (5).
(9). A vector bearing a gene according to (6).

DESCRIPTION OF THE DRAWINGS

FIG. 1 shows an illustrative example of an amino acid sequence of a pyrethrin biosynthetic enzyme of the present invention. (a) shows a typical example of an enzyme obtained from a pyrethrum flower, (b) shows an illustrative example of deletion of a signal sequence for translocation from the amino acid sequence of (a), and (c) and (d) show amino acid sequences, in which a further signal sequence for translocation is added to the sequence of (a). Meanwhile, underlined parts in (c) and (d) represent the signal sequence added to the sequence of (a).

On the other hand, (e), (f), (g), (h) severally designates amino acid sequences in which an amino acid of order number 6, 8, 103, 134, 227, 246, 249, 253, 359 in amino acid sequence of FIG. 1 is substituted.

As is described in a section of an embodiment of the invention, FIG. 1 (a) is a figure showing an amino acid sequence of Sequence No. 1, FIG. 1 (b) is a figure showing an amino acid sequence of Sequence No. 2, FIG. 1 (c) is a figure showing an amino acid sequence of Sequence No. 3, FIG. 1 (d) is a figure showing an amino acid sequence of Sequence No. 4, FIG. 1 (e) is a figure showing an amino acid sequence of Sequence No. 5, FIG. 1 (f) is a figure showing an amino acid sequence of Sequence No. 6, FIG. 1 (g) is a figure showing an amino acid sequence of Sequence No. 7, and FIG. 1 (h) is a figure showing an amino acid sequence of Sequence No. 8.

FIG. 2 shows sequences of a gene encoding the protein of the amino acid sequence of FIG. 1 (a) corresponding to a figure showing a base sequence of Sequence No. 9, and the amino acid sequence of FIG. 1 (e) corresponding to a figure showing a substitution sequence of Sequence No. 10, and the amino acid sequence of FIG. 1 (f) corresponding to a figure showing a substitution sequence of Sequence No. 11, and the amino acid sequence of FIG. 1 (g) corresponding to a figure showing a substitution sequence of Sequence No. 12, and the amino acid sequence of FIG. 1 (h) corresponding to a figure showing a substitution sequence of Sequence No. 13.

FIG. 2 (a) shows a sequence of a gene encoding the protein of the amino acid sequence of FIG. 1 (a), FIG. 2 (b) shows a sequence of a gene encoding the protein of the amino acid sequence of FIG. 1 (e), FIG. 2 (c) shows a sequence of a gene encoding the protein of the amino acid sequence of FIG. 1 (f), FIG. 2 (d) shows a sequence of a gene encoding the protein of the amino acid sequence of FIG. 1 (g), FIG. 2 (e) shows a sequence of a gene encoding the protein of the amino acid sequence of FIG. 1 (h).

FIG. 3 shows a chemical constitution formula and a list concretely indicating that structures of pyrethrins include side chains of chrysanthemic acid moiety ($R_1$) and rethrolone moiety ($R_2$).

FIG. 4 is a general formula of a chemical reaction showing that ester compounds in plant cells are biosynthesized by catalysis of acyltransferase from CoA thioester of carboxylic acid (acyl-CoA, RCO-S-CoA) and alcohol (R'—OH) as substrates.

FIG. 5 is a reaction formula showing an illustrative example of a pyrethrin biosynthetic reaction catalyzed by chrysanthemoyl group transferase.

FIG. 6 shows graphs of measurement results of pyrethrin biosynthetic enzyme activity with HPLC of Example 1. (a) and (b) show examples without and with enzyme activity at a protein purification step, respectively.

FIG. 7 is a list showing the procedure for enzyme production from a pyrethrum flower in Example 1.

FIG. 8 is an electrophoresis (SDS-PAGE) photo image to clarify the degree of molecular weight identification to confirm the degree of purification of a produced pyrethrin biosynthetic enzyme in Example 1.

FIG. 9 is an example of crude amino acid sequences obtained by analyzing each part of amino acids constructing a pyrethrin biosynthetic enzyme protein. (a) is a figure showing an amino acid sequence of Sequence No. 14, (b) is a figure showing an amino acid sequence of Sequence No. 15, and (c) is a figure showing an amino acid sequence of Sequence No. 16.

BEST MODES FOR CARRYING OUT THE INVENTION

Amino acid sequences based on extraction and separation of a pyrethrin biosynthetic enzyme, a process leading to a procedure of base sequence determination of the gene thereof, vectors bearing the gene based on the thus determined base sequence, and transformants introducing such vectors of the present invention are explained as follows. However, the above-described constitution of (1) to (9) is not limited to the following embodiments of the present invention, but embodiments that can be easily substituted and considered from such embodiments are also included.

It is essential to ensure proteins composing a pyrethrin biosynthetic enzyme in advance of the embodiment according to steps in order of the following (a) to (d).

Inventors of the present invention performed fractionation and purification of a pyrethrin biosynthetic enzyme using a crude enzyme solution prepared from a pyrethrum flower as a raw material, (1R)-trans-chrysanthemoyl-CoA and (S)-pyrethrolone as substrates to confirm an active function of the pyrethrin biosynthetic enzyme, and pyrethrin I synthesis activity as an indicator. In other words, as is described in the above (1), fractionation, crude purification and purification were performed in order of crude fractionation by ammonium sulfate precipitation, crude purification by batch method using hydrophobic resin, purification with anion-exchange chromatography, hydrophobic chromatography and gel filtration column, and enzyme reactions to the above-described substrate were performed at each step. An enzyme was obtained by fractionating purified fractions concluded to have pyrethrin biosynthetic enzyme activity. A protein band of a molecular weight 40,000, which is expected to contribute to esterification reaction as an enzyme, was detected by SDS-PAGE of the enzyme (FIG. 8).

A produced pyrethrin biosynthetic enzyme protein was successfully secured by transferring the protein obtained by confirming the above band onto a PVDF membrane.

Meanwhile, a specific process through confirmation of the above band is described later in Example 1.

(a) Analysis of Crude Amino Acid Sequences of Enzyme Protein

A purified enzyme secured as is described above was digested with trypsin, a protease, and fragmented into peptides. Then, digested peptide fragments were separated with HPLC, and amino acid residues of the separated peptides were singly disassembled and dissociated from the amino terminal end by the Edman method.

Amino acid residues were determined by analyzing produced phenylthiohydantoin derivatives with HPLC. This series of processes was performed using a peptide sequencer which is a special analytical instrument automated to repeat this reaction and analysis procedures.

As is described above, crude amino acid sequences constituting the pyrethrin biosynthetic enzyme protein were successfully obtained.

(b) Design of Primers and Determination for CDS.

Degenerate primers were designed based on base sequences estimated from determined amino acid sequences.

Unknown base sequences between known sequences were determined with PCR (Polymerase Chain Reaction) adopting the above primers (for example, four pairs of degenerate primers).

Next, a polynucleotide serving as an adaptor was previously added to DNA used as substrate of PCR. RACE-PCR was performed simultaneously using primers designed on an adaptor sequence and a known sequence, and DNA fragments containing sequences of both ends were amplified. The amplified DNA fragments were sequenced with DNA sequencer, and CDS was determined.

The CDS of the pyrethrin biosynthetic enzyme determined as is described above is shown in Sequence No. 9 of FIG. 2(a), as is described in above (5). Determination of a CDS No. 9 can also be achieved by other gene detection methods such as immunological screening methods for the above-described enzyme protein transferred onto a PVDF membrane, and hybridization method using nucleic acid probes as well as the above-described PCR.

(c) Determination for a Full-Length of Amino Acid Sequence

An amino acid sequence coded by the above-described gene corresponding to the above base sequence of Sequence No. 5 was determined.

An amino acid sequence of a pyrethrin biosynthetic enzyme determined in the present invention is shown in Sequence No. 1 of FIG. 1(a), as is described in the above (2).

Even though an amino acid sequence contains one or more of a substitution, deletion, insertion, and/or addition of an amino acid in the amino acid sequence of Sequence No. 1, the protein is included in proteins of a pyrethrin biosynthetic enzyme of the present invention as long as the protein can be extracted from plants containing the pyrethrin biosynthetic enzyme using similar techniques and process with an amino acid sequence of Sequence No. 1, and the protein exhibits a function as a pyrethrin biosynthetic enzyme, because the protein is able to function in the same manner as the enzyme protein shown as Sequence No. 1. Furthermore, as is described in (3), amino acid sequences according to the following sequences also correspond to the protein as a pyrethrin biosynthetic enzyme of the present invention:

A sequence shown as Sequence No. 2 in FIG. 1 (b): An amino acid sequence where a signal sequence for translocation (from N-terminal to Ser (S) 27 residue) was removed from the amino acid sequence of Sequence No. 1.

A sequence shown as Sequence No. 3 in FIG. 1 (c): An amino acid sequence where a histidine-tag and a linker sequence for expression in *E. coli* was added into the C-terminal.

A sequence shown as Sequence No. 4 in FIG. 1 (d): An amino acid sequence where GST sequence was added into the N-terminal to express the protein as glutathione S-transferase (GST) fusion protein in *E. coli*.

A sequence shown as Sequence No. 5 in FIG. 1 (e): An amino acid sequence where amino acid of order number of 6, 8, 103, 134, 227, 246, 249, 253, 359 of amino acid sequence in No. 1 is substituted as follows:

| Designation of sequence of amino acid | 6 | 8 | 103 | 134 | 227 | 246 | 249 | 253 | 359 |
|---|---|---|---|---|---|---|---|---|---|
| Amino acid sequence No. 1 | Ser | Arg | Asp | His | Ala | Thr | His | Gln | Tyr |
| Amino acid sequence No. 5 | Arg | Leu | Asp | Arg | Ala | Arg | His | Glu | Phe |

A sequence shown as Sequence No. 6 in FIG. 1 (f): An amino acid sequence where amino acid of order number of 6, 8, 103, 134, 227, 246, 249, 253, 359 of amino acid sequence in No. 1 is substituted as follows:

| Designation of sequence of amino acid | 6 | 8 | 103 | 134 | 227 | 246 | 249 | 253 | 359 |
|---|---|---|---|---|---|---|---|---|---|
| Amino acid sequence No. 1 | Ser | Arg | Asp | His | Ala | Thr | His | Gln | Tyr |
| Amino acid sequence No. 6 | Arg | Leu | Asp | Arg | Thr | Arg | Gln | Gln | Phe |

A sequence shown as Sequence No. 7 in FIG. 1 (g): An amino acid sequence where amino acid of order number of 6, 8, 103, 134, 227, 246, 249, 253, 359 of amino acid sequence in No. 1 is substituted as follows:

| Designation of sequence of amino acid | 6 | 8 | 103 | 134 | 227 | 246 | 249 | 253 | 359 |
|---|---|---|---|---|---|---|---|---|---|
| Amino acid sequence No. 1 | Ser | Arg | Asp | His | Ala | Thr | His | Gln | Tyr |
| Amino acid sequence No. 7 | Arg | Leu | Asp | Arg | Thr | Arg | Gln | Gln | Tyr |

A sequence shown as Sequence No. 8 in FIG. 1 (h): An amino acid sequence where amino acid of order number of 6, 8, 103, 134, 227, 246, 249, 253, 359 of amino acid sequence in No. 1 is substituted as follows:

| Designation of sequence of amino acid | 6 | 8 | 103 | 134 | 227 | 246 | 249 | 253 | 359 |
|---|---|---|---|---|---|---|---|---|---|
| Amino acid sequence No. 1 | Ser | Arg | Asp | His | Ala | Thr | His | Gln | Tyr |
| Amino acid sequence No. 8 | Arg | Leu | Tyr | Arg | Thr | Arg | Gln | Gln | Tyr |

As is described later in Example 1, an amino acid sequence shown as Sequence No. 2 is extracted from a pyrethrum flower, therefore it can be naturally purified. Enzymes according to amino acid sequences shown as Sequence Nos. 3 and 4 were obtained by introduction of a vector bearing a sequence encoding the amino acid sequence of Sequence No. 1 into *E. coli* and expression of the protein in *E. coli*. However, when an enzyme can be expressed in *E. coli* as a host, it is highly expected that the enzyme also actually exists as a pyrethrin biosynthetic enzyme in plants, which is able to produce pyrethrin. If the enzyme exists, the enzyme can be obviously extracted and purified from the above plant body using similar techniques and process with the amino acid sequence of Sequence No. 2.

Because protein according to the amino acid sequence of above (2) having activity for pyrethrin biosynthesis exerts the same function as such a protein as well as protein according to the amino acid sequence of Sequence No. 1, and included as a producible protein in the technical concept and the scope of the present invention, the gene of the present invention also consequently includes not only the above gene of (4) coding amino acid sequence shown as Sequence No. 1 but also the genes of above (5) encoding the above protein of (2) into the technical concept of the present invention. Furthermore, the gene of above (6) encoding a protein of amino acid sequences of the Sequence Nos. 2, 3, and 4 of above (3) is also included in the technical concept of the present invention.

Moreover, as is after described in experiment 2, we can easily prospect that the amino acid sequence in Sequence No. 5 or Sequence No. 6 or Sequence No. 7 or Sequence No. 8 may have enzyme activity for smooth pyrethrin biosynthesis according to experiences of substitution of amino acid wherein amino acid sequence No. 1 is substituted into an amino acid Sequence No. 5, 6, 7, 8 according to following list as is designated by FIG. 1 (e), (f), (g),(h).

| Designation of sequence of | Order number of amino acid sequence | | | | | | | | |
|---|---|---|---|---|---|---|---|---|---|
| amino acid | 6 | 8 | 103 | 134 | 227 | 246 | 249 | 253 | 359 |
| Amino acid sequence No. 1 | Ser | Arg | Asp | His | Ala | Thr | His | Gln | Tyr |
| Amino acid sequence No. 5 | Arg | Leu | Asp | Arg | Ala | Arg | His | Glu | Phe |
| Amino acid sequence No. 6 | Arg | Leu | Asp | Arg | Thr | Arg | Gln | Gln | Phe |
| Amino acid sequence No. 7 | Arg | Leu | Asp | Arg | Thr | Arg | Gln | Gln | Tyr |
| Amino acid sequence No. 8 | Arg | Leu | Tyr | Arg | Thr | Arg | Gln | Gln | Tyr |

An amino acid sequence database of known proteins was searched for sequences similar to Sequence No. 1. As a result, such a sequence was not a predicted known acyltransferase, however, some GDSL-motif lipases were similar to the amino acid sequence. Therefore, the above pyrethrin biosynthetic enzyme proteins of (2) and (3) are expected to be proteins similar to GDSL-motif lipase.

In order to confirm biosynthesis activity of the pyrethrin biosynthetic enzyme genes of above (4), (5), and (6), it is appropriate for example, to insert these genes into a vector DNA first, introduce the same to E. coli, express the pyrethrin biosynthetic enzymes as a fusion protein with a histidine-tag in E. coli, purify the expressed pyrethrin biosynthetic enzyme with Ni-NTA affinity chromatography, and then evaluate activity using (1R)-trans-chrysanthemoyl-CoA and (S)-pyrethrolone as a substrate and pyrethrin I synthesis activity as an indicator.

(d) Production of Vector and Transformants Introducing the Vector

The vector of above (7) is produced by inserting any of the genes of above (4), (5), and (6), and exhibits pyrethrin biosynthetic enzyme activity. The above vector can express the inserted gene or gene fragment into hosts such as plants and microorganisms by being introduced into the hosts by well-known transformation methods.

Also, a transformant having the vector of above (7) introduced therein refers to a transformant which introduces a gene or gene fragment related to pyrethrin biosynthesis into a host. A term of "having the above vector introduced" used herein refers to that the gene inserted into the vector is introduced into a host in the manner capable of expressing such a gene using well-known genetic engineering techniques.

Methods for introducing genes include, but are not limited to, a transformation method with Agrobacterium, a particle gun method, a microinjection method and an electroporation method.

When the transformation method with Agrobacterium is used, the relevant gene is inserted into a Ti plasmid vector, the vector is introduced into Agrobacterium, and then the Agrobacterium is infected to the appropriate plant. A tumor (crown gall) is formed at the site of gene introduction. After elimination of Agrobacterium, many plant bodies regenerated from the crown gall are evaluated on activity, and plant bodies that highly express the pyrethrin biosynthetic enzyme can be selected.

Such transformants can express genes related to pyrethrin biosynthesis in their bodies. Therefore, a pyrethrin biosynthetic enzyme may be produced in large quantities by constructing transformants, which have the vector of above (7) bearing a promoter to express such an enzyme in large quantity by using bacterial chromosome and/or chloroplast of plants, blue-green algae, yeasts, or bacteria such as E. coli as a host.

Since the above-described vector contains a gene (or a gene fragment) of a pyrethrin biosynthetic enzyme derived from pyrethrum, plant chromosome and/or chloroplast are preferred as hosts for construction of transformants, in particular, chromosome and/or chloroplast of asteracea plants, which belong to the same family as pyrethrum, are more preferable. Such asteracea plants include, but are not limited to, marigold, African marigold, calendula and zinnia.

Above-described plants also include not only entire plant bodies but also a part of the plant bodies, for example, a leaf, seed, tuber, graft and the like. Furthermore, the above plants also include plant materials (a part of a plant including the flower, stem, fruit, leaf, and root) with growth potential, such as plant tissue, protoplast, cell, callus, organs, plant seed, germ, pollen, ovum, and zygote, derived from genetically-modified plants and progeny thereof transformed previously.

Pyrethrin can be produced by using either one of the protein of above (2) or the above transformants. The present invention provides such a pyrethrin production method. According to the method, pyrethrin can be produced effectively and easily using the above asteracea plants or other plants with obviously faster growth than pyrethrum, and thus, social demand seeking safe and environment-friendly insecticide could be greatly fulfilled by the present invention.

EXAMPLES

Hereinafter, details of the present invention will be concretely described by referring to Examples as follows.

Example 1

An enzyme was purified from pyrethrum flowers according to procedures shown in FIG. 7 to analyze the above-described amino acid sequence of (a).

Detailed explanations regarding the procedures are provided below.

Buffer Compositions Used for Purification

Compositions of buffers used for purification are shown in Tables 1 to 6.

TABLE 1

| Buffer A | |
|---|---|
| Constituent | Concentration (mM) |
| Tris-HCl, pH 8.0 | 50 |
| EDTA | 1 |
| DTT | 5 |
| Sodium Ascorbate | 100 |
| PMSF | 2 |

TABLE 2

| Buffer B | |
|---|---|
| Constituent | Concentration (mM) |
| Tris-HCl, pH 8.0 | 20 |
| EDTA | 1 |
| DTT | 5 |

TABLE 3

| Buffer C | |
|---|---|
| Constituent | Concentration (mM) |
| Tris-HCl, pH 8.0 | 20 |
| EDTA | 1 |
| DTT | 5 |
| NaCl | 500 |

TABLE 4

| Buffer D | |
|---|---|
| Constituent | Concentration (mM) |
| Tris-HCl, pH 8.0 | 20 |
| EDTA | 1 |
| DTT | 5 |
| NaCl | 150 |

TABLE 5

| Buffer E | |
|---|---|
| Constituent | Concentration (mM) |
| Tris-HCl, pH 8.0 | 20 |
| EDTA | 1 |
| DTT | 5 |
| $(NH_4)_2SO_4$ | 400 |

TABLE 6

| Buffer F | |
|---|---|
| Constituent | Concentration (mM) |
| Tris-HCl, pH 8.0 | 50 |
| EDTA | 1 |

TABLE 6-continued

| Buffer F | |
|---|---|
| Constituent | Concentration (mM) |
| DTT | 5 |
| Sodium Ascorbate | 100 |
| $(NH_4)_2SO_4$ | 1000 |

Reaction of Pyrethrin Biosynthetic Enzyme

An enzyme reaction was assayed in each purification step, and enzyme activity of a pyrethrin biosynthetic enzyme in purified fractions was evaluated. A reaction was performed at 25° C. for 1 hour using the reaction composition shown in Table 7 as follows. After the enzyme reaction, 200 μl of hexane was added to the reaction solution. The organic phase was separated and collected therefrom, and 10 μl for each sample was used for HPLC analysis.

TABLE 7

| Composition for reaction of pyrethrin biosynthetic enzyme | | |
|---|---|---|
| | Volume (μl) | Concentration (mM) |
| Enzyme solution | 20 | |
| (1R)-trans-Chrysanthemoyl-CoA (10 mM aqueous solution) | 10 | 0.5 |
| (S)-Pyrethrolone (20 mM DMSO solution) | 4 | 1 |
| 250 mM Tris-HCl (pH 7.5), 1 mM EDTA | 40 | |
| Water | 126 | 50 |
| Total volume | 200 | |

Activity Measurement of Pyrethrin Biosynthesis Enzyme with HPLC

HPLC analysis was performed using SCL-10A VP (programming unit), DGU-14A (deaeration unit), LC-6AD (pump), CTO-10AS VP (sample injection and column oven unit), and SPD-10AV VP (optical detector) produced by SHIMADZU, and data were processed with CLASS-VP software from SHIMADZU. A Cadenza C-18 column from IMTAKT (0.46 cm I.D.×10 cm L.) was used, and absorption at 230 nm was measured at 40° C., at a flow rate of 1 ml/min. Acetonitrile:$H_2O$ (65:35) was used as mobile phase.

HPLC analysis results are exemplified in FIG. 6. Results of fractions without and with enzyme activity at the protein purification step are shown in FIGS. 6 (a) and (b), respectively. As indicated in the figure, a peak of pyrethrin I was detected with 4.9 min of retention time in the course of elution time when the fractionated solution contains the enzyme.

Preparation of Crude Enzyme

A crude enzyme was prepared from 500 g of pyrethrum flower buds according to the following procedures. Ice cold 1.5 L of Buffer A and polyvinyl pyrrolidone (1/10 volume (w/v) of Buffer A) were added to the buds, and the buds were homogenized using a blender. A homogenate was filtered with a four-layered cheesecloth, and filtrate was centrifuged at 8,000×g for 20 min at 4° C. Collected supernatant was mixed with 100 mL of DOWEX (1×4, 100-200 Cl FORM) (Muromachi technos CO., LTD), stirred with a stirrer for 10 min, and centrifuged at 8,000×g for 20 min at 4° C. Supernatant was collected as a crude enzyme solution, and provided for further purification.

Fractionation by Ammonium Sulfate Precipitation

Ammonium sulfate was ground using a pestle and a mortar in advance, and resolved and mixed using a stirrer by portions into the crude enzyme solution obtained by the above-described preparation to a concentration of 30% saturation of ammonium sulfate. After allowing it to stand for 30 min, the solution was centrifuged at 8,000×g for 20 min at 4° C. (g represents gravitational acceleration). Supernatant was collected, and ammonium sulfate was added so that a concentration of ammonium sulfate becomes 80% saturation. After allowing it to stand for one night, the solution was centrifuged at 8,000×g for 20 min at 4° C. and the enzyme fraction was obtained as precipitate.

Crude Purification by Batch Method Using Hydrophobic Resin

The precipitate obtained by the above-described fractionation was suspended into Buffer F, and Phenyl Sepharose (GE Healthcare) was added to the solution. After mixing using a stirrer for 30 min, the mixture was separated using a Buchner funnel. Phenyl Sepharose remaining in the Buchner funnel was washed with 500 mL of Buffer F, and then protein absorbed by the resin was eluted with 500 mL of Buffer B. Ammonium sulfate was added into the collected elute to 1 M of concentration, and then 20 mL of Phenyl Sepharose (GE Healthcare) was added to the solution. After mixing using a stirrer for 30 min, the mixture was transferred and settled in Econo-Column (Bio-Rad), protein absorbed by the resin was eluted with 50 mL of Buffer B. Eluate was transferred into a cellophane dialysis tubing, dialyzed in 2 L of desalting buffer for 2 hours by stirring the buffer using a stirrer, and followed by another desalting after buffer change for 3 hours. The desalted enzyme solution was further purified by column chromatography using an AKTA explorer (GE Healthcare) system.

Purification with Anion-Exchange Chromatography

The enzyme solution obtained by the above-described crude purification with the batch method was further purified by anion-exchange chromatography using a Q Sepharose column according to the following conditions.

TABLE 8

| System | ÄKTA explorer 10 s |
|---|---|
| Column | HiPrep ™ 16/10 Q FF (GE Healthcare) |
| Pump A | Buffer B |
| Pump B | Buffer C |
| Equilibration | (A) 100% |
| Sample | Desalted enzyme solution after batch treatment with Phenyl Sepharose |
| Rinse | (A) 100%, 100 mL |
| Elution | (B) 0-100% in 400 mL |
| Flow rate | 4 mL/min |
| Fraction | 10 mL/tube |

Purification with Hydrophobic Chromatography

The enzyme solution obtained by the above-described anion-exchange chromatography was further purified by hydrophobic chromatography using a Phenyl Superose column according to the following conditions.

TABLE 9

| System | ÄKTA explorer 10 s |
|---|---|
| Column | Phenyl Superose FPLC ® (GE Healthcare) |
| Pump A | Buffer E |
| Pump B | Buffer B |
| Equilibration | (A) 100%, 10 mL |
| Sample | Enzyme solution purified with anion-exchange chromatography |
| Rinse | (A) 100% |
| Elution | (B) 0-100% in 20 mL |
| Flow rate | 0.4 mL/min |
| Fraction | 2 mL/tube |

Purification with Gel Filtration

The enzyme solution obtained by the above-described hydrophobic chromatography was further purified by gel filtration using a Superdex 75 column according to the following conditions.

TABLE 10

| System | ÄKTA explorer 10 s |
|---|---|
| Column | Superdex 75 HR 10/30 (GE Healthcare) |
| Buffer | Buffer D |
| Sample | Active fractions purified with Phenyl Sepharose |
| Flow rate | 0.5 mL/min |
| Fraction | 0.5 mL/tube |

An enzyme purified by the above-described methods was separated with SDS-PAGE, and the degree of purification was confirmed with silver staining. The result of silver staining is shown in FIG. 8. A single protein band of the pyrethrin biosynthetic enzyme with a molecular weight of approximately 40,000 was detected.

Example 2

Procedures from analysis of the above-described crude amino acid sequence (a) or (b) to determination of a full length amino acid sequence of the pyrethrin biosynthetic enzyme obtained in Example 1, further, preparation of transformant introducing a vector bearing a gene, which codes protein of the above-described amino acid sequence, were performed as follows.

Analysis of Amino Acid Segments including Pyrethrin Biosynthetic Enzyme Protein

The protein band obtained in Example 1 was excised from a gel, and used as a sample for analysis of an internal amino acid sequence. Also, the band of an SDS-PAGE was transferred to a PVDF membrane, detected with Coomassie Blue staining, and the excised band was used for N-terminal amino acid analysis. This series of manipulations was performed according to well-known methods.

As a result of the above-described amino acid analyses, examples of crude amino acid sequences, Sequence Nos. 14, 15 and 16, including the enzyme protein shown in FIGS. 9 (*a*), (*b*) and (*c*) were confirmed, respectively.

Design of Primers and Determination of a CDS

A CDS (FIG. 2 (*a*), Sequence No. 9) and amino acid sequence (FIG. 1 (*a*), Sequence No. 1) were determined according to the above-described methods based on amino acid sequences determined by amino acid analyses. Methods used in this series of manipulations, including cDNA preparation, PCR, and sequence analysis using DNA sequencer, were performed according to well-known methods.

Similarly a CDS (FIG. 2 (*b*), Sequence No. 10) and amino acid sequence (FIG. 1 (*e*), Sequence No. 5), and a CDS (FIG. 2 (*c*), Sequence No. 11) and amino acid sequence (FIG. 1 (*f*), Sequence No. 6), a CDS (FIG. 2 (*d*), Sequence No. 12) and amino acid sequence (FIG. 1 (*g*), Sequence No. 7), a CDS (FIG. 2 (*e*), Sequence No. 13) and amino acid sequence (FIG. 1 (*h*), Sequence No. 8) may be determined, according to the above-described methods based on amino acid sequences determined by amino acid analyses, according to the experience of substitution.

Determination for a Full-Length of Amino Acid Sequence

The N-terminal amino acid sequence of the pyrethrin biosynthetic enzyme determined by the above analysis is a sequence without a portion from the N-terminal to serine (S) 27 of the amino acid sequence of Sequence No. 1, as shown in FIG. 1 (*b*), Sequence No. 2. And, as is described above, while the truncated amino acid sequence shown in Sequence No. 2 corresponds to the sequence for the protein, which has enzyme activity in pyrethrum, the removed 27 amino acid residues are a signal sequence for translocation, which has a function to ensure conditions for smooth pyrethrin biosynthesis. Therefore, the sequence of FIG. 1 (a) including the above 27 amino acid residues, i.e., amino acid sequence of Sequence No. 1, corresponds to the sequence of the pyrethrin biosynthetic enzyme including such a signal sequence for translocation.

Meanwhile, a protein with amino acid sequences of Sequence Nos. 3 and 4 is obtained by abundant expression of a gene encoding a protein with amino acid sequence of Sequence No. 1, which are integrated into a vector and introduced into E. coli. It has already been pointed out in an embodiment (c) of the present invention that this protein has a high possibility of having activity of a pyrethrin biosynthetic enzyme and to exist in plants, which is capable of producing pyrethrin.

Moreover, as is after described in experiment 2, we can easily prospect that the amino acid sequence in Sequence No. 5 or Sequence No. 6 or Sequence No. 7 or Sequence No. 8 may have enzyme activity for smooth pyrethrin biosynthesis according to experiences of substitution of amino acid wherein amino acid sequence No. 1 is substituted into an amino acid Sequence No. 5, 6, 7, 8 according to following list as is designated by FIG. 1 (e), (f), (g),(h).

| Designation of sequence of | Order number of amino acid sequence | | | | | | | | |
|---|---|---|---|---|---|---|---|---|---|
| amino acid | 6 | 8 | 103 | 134 | 227 | 246 | 249 | 253 | 359 |
| Amino acid sequence No. 1 | Ser | Arg | Asp | His | Ala | Thr | His | Gln | Tyr |
| Amino acid sequence No. 5 | Arg | Leu | Asp | Arg | Ala | Arg | His | Glu | Phe |
| Amino acid sequence No. 6 | Arg | Leu | Asp | Arg | Thr | Arg | Gln | Gln | Phe |
| Amino acid sequence No. 7 | Arg | Leu | Asp | Arg | Thr | Arg | Gln | Gln | Tyr |
| Amino acid sequence No. 8 | Arg | Leu | Tyr | Arg | Thr | Arg | Gln | Gln | Tyr |

Production of Vector and Transformant

Construction of vector and transformant bearing the above-described pyrethrin biosynthetic enzyme gene were performed as follows.

Available vector in the present invention includes existing vectors used for transformation of microorganisms, plants, and plant cells. It is substantially predictable based on common knowledge of one skilled in the art that such vectors are able to contain a constitutive or inducible promoter to express known genes; a protein of facilitating solubilization and purification of expressed protein such as a histidine-tag, glutathione S-transferase; fusion protein such as maltose-binding protein; a drug resistance gene facilitating selection of transformants, and replication origins for binary vector system of Agrobacterium in addition to a part of the above full length gene encoding the above pyrethrin biosynthetic enzyme.

Specifically, for example, pET vector (Novagen), pGEX vector (GE Healthcare), and pMAL vector (New England Biolab) can be used for introduction to microorganisms such as E. coli. Vectors appropriate for introduction into plants with Agrobacterium include pBI101 and pBI121. There is no specific limitation on the type of vectors when the vector is introduced into plant cells by electroporation or particle gun method. Also, the above drug resistance genes include resistance genes of ampicillin, kanamycin and hygromycin. As examples of the above promoters, 35S promoter derived from a cauliflower mosaic virus (constitutive promoter) or promoters of heat shock-induced proteins (inducible promoter) can be used. Replication origins include replication origins derived from Ti or Ri plasmids. It is substantially predictable that construction of these transformants is feasible based on common knowledge of one skilled in the art.

When the above-described transformants are constructed with microorganisms such as E. coli and yeast, conversion of a substance using a microbial cell system becomes possible. Furthermore, construction of the above-described transformants using asteracea plants such as African marigold, calendula and zinnia, which are known to produce a small amount of pyrethrin for less than practical use, and improvement in ability of pyrethrin synthesis enable effective production of pyrethrin in plants which grow faster than pyrethrum. Thus, this is useful for production of insecticides.

EFFECT OF THE INVENTION

The present invention discloses amino acid sequences of enzymes related to pyrethrin biosynthesis and a base sequence of a gene thereof, and thus provides perspective that highly useful and safe pyrethrin as a raw material of insecticides can be inexpensively and effectively produced by using fast growing plants. Therefore, this indicates a possibility that the present invention can make a great contribution to the insecticide industry.

Furthermore, the present invention can be used in all industrial areas using pyrethroids for insecticides, in particular, the area of insecticidal instruments and devices using pyrethroids as active ingredients, such as mosquito/fly coils, insecticide sprays, heat and transpiration devices for liquid insecticides, and electrothermal mosquito mats.

What is claimed is:

1. An isolated polynucleotide consisting of the nucleotide sequence set forth in SEQ ID NO: 11.

2. A vector comprising the isolated polynucleotide of claim 1.

3. A recombinant cell comprising the vector of claim 2.

4. A vector comprising an isolated polynucleotide encoding a protein consisting of the amino acid sequence set forth in SEQ ID NO: 5.

5. A recombinant cell comprising the vector of claim 4.

* * * * *

SEQUENCE LISTING

<160> NUMBER OF SEQ ID NOS: 16

<210> SEQ ID NO 1
<211> LENGTH: 365
<212> TYPE: PRT
<213> ORGANISM: Pyrethrum Cinerariifolium -continued

```
<400> SEQUENCE: 1

Met Ala Val Ala Ser Ser Lys Arg Gly Ala Leu Val Leu Val Ala
1               5                   10                  15

Val Leu Cys Leu Ser Leu Pro Thr Gly Cys Leu Ser Ser Gln Gln
                20                  25                  30

Ala Ala Ala Leu Phe Ile Phe Gly Asp Ser Val Phe Asp Pro Gly
                35                  40                  45

Asn Asn Asn His Ile Asn Thr His Val Asn Phe Lys Ala Asn Phe
                50                  55                  60

Trp Pro Tyr Gly Gln Ser Tyr Phe Ser Pro Thr Gly Arg Phe
                65                  70                  75

Ser Asp Gly Arg Ile Ile Pro Asp Phe Ile Ala Glu Tyr Ala Ser
                80                  85                  90

Leu Pro Ile Ile Pro Ala Tyr Leu Glu Pro Asn Asn Asp Phe Thr
                95                  100                 105

His Gly Ala Asn Phe Ala Ser Ala Gly Ala Gly Ala Leu Ile Ala
                110                 115                 120

Ser His Ala Gly Leu Ala Val Gly Leu Gln Thr Gln Leu His Tyr
                125                 130                 135

Phe Gly Asp Leu Val Asp His Tyr Arg Gln Asn Leu Gly Asp Ile
                140                 145                 150

Lys Ser Arg Gln Leu Leu Ser Asp Ala Val Tyr Leu Phe Ser Cys
                155                 160                 165

Gly Gly Asn Asp Tyr Gln Ser Pro Tyr Pro Tyr Thr Gln Glu
                170                 175                 180

Gln Tyr Val Asp Ile Val Ile Gly Asn Met Thr Asn Val Ile Lys
                185                 190                 195

Gly Ile Tyr Glu Lys Gly Gly Arg Lys Phe Gly Val Val Asn Val
                200                 205                 210

Pro Leu Ile Gly Cys Trp Pro Gly Met Arg Ala Lys Gln Pro Gly
                215                 220                 225

Asn Ala Cys Asn Thr Glu Val Asp Glu Leu Thr Arg Leu His Asn
                230                 235                 240

Gln Ala Phe Ala Lys Thr Leu Glu His Leu Glu Lys Gln Leu Glu
                245                 250                 255

Gly Phe Val Tyr Ala Lys Phe Asp Leu Ser Thr Ala Ile Leu Asn
                260                 265                 270

Arg Met Lys Asn Pro Ser Lys Tyr Gly Phe Lys Glu Gly Glu Ser
                275                 280                 285

Ala Cys Cys Gly Ser Gly Pro Phe Gly Gly Asn Tyr Asp Cys Gly
                290                 295                 300

Arg Ile Lys Glu Phe Gly Leu Cys Asp Asn Ala Thr Glu Tyr Phe
                305                 310                 315

Phe Phe Asp Pro Phe His Pro Asn Glu Leu Ala Ser Arg Gln Phe
                320                 325                 330

Ala Glu Met Phe Trp Asp Gly Asp Ser Met Val Thr Gln Pro Tyr
                335                 340                 345

Asn Leu Lys Ala Leu Phe Glu Gly Lys Pro Ser Thr Lys Tyr Leu
                350                 355                 360

Pro Asn Asp Glu Leu
                365
```

```
<210> SEQ ID NO 2
<211> LENGTH: 338
<212> TYPE: PRT
<213> ORGANISM: Pyrethrum Cinerariifolium

<400> SEQUENCE: 2

Ser Gln Gln Ala Ala Leu Phe Ile Phe Gly Asp Ser Val Phe
1               5                   10                  15

Asp Pro Gly Asn Asn Asn His Ile Asn Thr His Val Asn Phe Lys
                20                  25                  30

Ala Asn Phe Trp Pro Tyr Gly Gln Ser Tyr Phe Ser Ser Pro Thr
                35                  40                  45

Gly Arg Phe Ser Asp Gly Arg Ile Ile Pro Asp Phe Ile Ala Glu
                50                  55                  60

Tyr Ala Ser Leu Pro Ile Ile Pro Ala Tyr Leu Glu Pro Asn Asn
                65                  70                  75

Asp Phe Thr His Gly Ala Asn Phe Ala Ser Ala Gly Ala Gly Ala
                80                  85                  90

Leu Ile Ala Ser His Ala Gly Leu Ala Val Gly Leu Gln Thr Gln
                95                  100                 105

Leu His Tyr Phe Gly Asp Leu Val Asp His Tyr Arg Gln Asn Leu
                110                 115                 120

Gly Asp Ile Lys Ser Arg Gln Leu Leu Ser Asp Ala Val Tyr Leu
                125                 130                 135

Phe Ser Cys Gly Gly Asn Asp Tyr Gln Ser Pro Tyr Tyr Pro Tyr
                140                 145                 150

Thr Gln Glu Gln Tyr Val Asp Ile Val Ile Gly Asn Met Thr Asn
                155                 160                 165

Val Ile Lys Gly Ile Tyr Glu Lys Gly Arg Lys Phe Gly Val
                170                 175                 180

Val Asn Val Pro Leu Ile Gly Cys Trp Pro Gly Met Arg Ala Lys
                185                 190                 195

Gln Pro Gly Asn Ala Cys Asn Thr Glu Val Asp Glu Leu Thr Arg
                200                 205                 210

Leu His Asn Gln Ala Phe Ala Lys Thr Leu Glu His Leu Glu Lys
                215                 220                 225

Gln Leu Glu Gly Phe Val Tyr Ala Lys Phe Asp Leu Ser Thr Ala
                230                 235                 240

Ile Leu Asn Arg Met Lys Asn Pro Ser Lys Tyr Gly Phe Lys Glu
                245                 250                 255

Gly Glu Ser Ala Cys Cys Gly Ser Gly Pro Phe Gly Gly Asn Tyr
                260                 265                 270

Asp Cys Gly Arg Ile Lys Glu Phe Gly Leu Cys Asp Asn Ala Thr
                275                 280                 285

Glu Tyr Phe Phe Phe Asp Pro Phe His Pro Asn Glu Leu Ala Ser
                290                 295                 300

Arg Gln Phe Ala Glu Met Phe Trp Asp Gly Asp Ser Met Val Thr
                305                 310                 315

Gln Pro Tyr Asn Leu Lys Ala Leu Phe Glu Gly Lys Pro Ser Thr
                320                 325                 330

Lys Tyr Leu Pro Asn Asp Glu Leu
                335
```

```
<210> SEQ ID NO 3
<211> LENGTH: 376
<212> TYPE: PRT
<213> ORGANISM: Pyrethrum Cinerariifolium

<400> SEQUENCE: 3

Met Ala Val Ala Ser Ser Lys Arg Gly Ala Leu Val Leu Val Ala
1               5                   10                  15

Val Leu Cys Leu Ser Leu Pro Thr Gly Cys Leu Ser Ser Gln Gln
                20                  25                  30

Ala Ala Ala Leu Phe Ile Phe Gly Asp Ser Val Phe Asp Pro Gly
                35                  40                  45

Asn Asn Asn His Ile Asn Thr His Val Asn Phe Lys Ala Asn Phe
                50                  55                  60

Trp Pro Tyr Gly Gln Ser Tyr Phe Ser Ser Pro Thr Gly Arg Phe
                65                  70                  75

Ser Asp Gly Arg Ile Ile Pro Asp Phe Ile Ala Glu Tyr Ala Ser
                80                  85                  90

Leu Pro Ile Ile Pro Ala Tyr Leu Glu Pro Asn Asn Asp Phe Thr
                95                  100                 105

His Gly Ala Asn Phe Ala Ser Ala Gly Ala Gly Ala Leu Ile Ala
                110                 115                 120

Ser His Ala Gly Leu Ala Val Gly Leu Gln Thr Gln Leu His Tyr
                125                 130                 135

Phe Gly Asp Leu Val Asp His Tyr Arg Gln Asn Leu Gly Asp Ile
                140                 145                 150

Lys Ser Arg Gln Leu Leu Ser Asp Ala Val Tyr Leu Phe Ser Cys
                155                 160                 165

Gly Gly Asn Asp Tyr Gln Ser Pro Tyr Tyr Pro Tyr Thr Gln Glu
                170                 175                 180

Gln Tyr Val Asp Ile Val Ile Gly Asn Met Thr Asn Val Ile Lys
                185                 190                 195

Gly Ile Tyr Glu Lys Gly Gly Arg Lys Phe Gly Val Val Asn Val
                200                 205                 210

Pro Leu Ile Gly Cys Trp Pro Gly Met Arg Ala Lys Gln Pro Gly
                215                 220                 225

Asn Ala Cys Asn Thr Glu Val Asp Glu Leu Thr Arg Leu His Asn
                230                 235                 240

Gln Ala Phe Ala Lys Thr Leu Glu His Leu Glu Lys Gln Leu Glu
                245                 250                 255

Gly Phe Val Tyr Ala Lys Phe Asp Leu Ser Thr Ala Ile Leu Asn
                260                 265                 270

Arg Met Lys Asn Pro Ser Lys Tyr Gly Phe Lys Glu Gly Glu Ser
                275                 280                 285

Ala Cys Cys Gly Ser Gly Pro Phe Gly Gly Asn Tyr Asp Cys Gly
                290                 295                 300

Arg Ile Lys Glu Phe Gly Leu Cys Asp Asn Ala Thr Glu Tyr Phe
                305                 310                 315

Phe Phe Asp Pro Phe His Pro Asn Glu Leu Ala Ser Arg Gln Phe
                320                 325                 330

Ala Glu Met Phe Trp Asp Gly Asp Ser Met Val Thr Gln Pro Tyr
                335                 340                 345

Asn Leu Lys Ala Leu Phe Glu Gly Lys Pro Ser Thr Lys Tyr Leu
                350                 355                 360
```

-continued

```
Pro Asn Asp Glu Leu Ala Ala Leu Glu His His His His
                365                 370                 375
His

<210> SEQ ID NO 4
<211> LENGTH: 599
<212> TYPE: PRT
<213> ORGANISM: Pyrethrum Cinerariifolium

<400> SEQUENCE: 4

Met Ser Pro Ile Leu Gly Tyr Trp Lys Ile Lys Gly Leu Val Gln
  1               5                  10                  15

Pro Thr Arg Leu Leu Leu Glu Tyr Leu Glu Glu Lys Tyr Glu Glu
                 20                  25                  30

His Leu Tyr Glu Arg Asp Glu Gly Asp Lys Trp Arg Asn Lys Lys
                 35                  40                  45

Phe Glu Leu Gly Leu Glu Phe Pro Asn Leu Pro Tyr Tyr Ile Asp
                 50                  55                  60

Gly Asp Val Lys Leu Thr Gln Ser Met Ala Ile Ile Arg Tyr Ile
                 65                  70                  75

Ala Asp Lys His Asn Met Leu Gly Gly Cys Pro Lys Glu Arg Ala
                 80                  85                  90

Glu Ile Ser Met Leu Glu Gly Ala Val Leu Asp Ile Arg Tyr Gly
                 95                 100                 105

Val Ser Arg Ile Ala Tyr Ser Lys Asp Phe Glu Thr Leu Lys Val
                110                 115                 120

Asp Phe Leu Ser Lys Leu Pro Glu Met Leu Lys Met Phe Glu Asp
                125                 130                 135

Arg Leu Cys His Lys Thr Tyr Leu Asn Gly Asp His Val Thr His
                140                 145                 150

Pro Asp Phe Met Leu Tyr Asp Ala Leu Asp Val Val Leu Tyr Met
                155                 160                 165

Asp Pro Met Cys Leu Asp Ala Phe Pro Lys Leu Val Cys Phe Lys
                170                 175                 180

Lys Arg Ile Glu Ala Ile Pro Gln Ile Asp Lys Tyr Leu Lys Ser
                185                 190                 195

Ser Lys Tyr Ile Ala Trp Pro Leu Gln Gly Trp Gln Ala Thr Phe
                200                 205                 210

Gly Gly Gly Asp His Pro Pro Lys Ser Asp Leu Glu Val Leu Phe
                215                 220                 225

Gln Gly Pro Leu Gly Ser Pro Glu Phe Met Ala Val Ala Ser Ser
                230                 235                 240

Lys Arg Gly Ala Leu Val Leu Val Ala Val Leu Cys Leu Ser Leu
                245                 250                 255

Pro Thr Gly Cys Leu Ser Ser Gln Gln Ala Ala Ala Leu Phe Ile
                260                 265                 270

Phe Gly Asp Ser Val Phe Asp Pro Gly Asn Asn Asn His Ile Asn
                275                 280                 285

Thr His Val Asn Phe Lys Ala Asn Phe Trp Pro Tyr Gly Gln Ser
                290                 295                 300

Tyr Phe Ser Ser Pro Thr Gly Arg Phe Ser Asp Gly Arg Ile Ile
                305                 310                 315

Pro Asp Phe Ile Ala Glu Tyr Ala Ser Leu Pro Ile Ile Pro Ala
                320                 325                 330
```

```
Tyr Leu Glu Pro Asn Asn Asp Phe Thr His Gly Ala Asn Phe Ala
                335                 340                 345

Ser Ala Gly Ala Gly Ala Leu Ile Ala Ser His Ala Gly Leu Ala
                350                 355                 360

Val Gly Leu Gln Thr Gln Leu His Tyr Phe Gly Asp Leu Val Asp
                365                 370                 375

His Tyr Arg Gln Asn Leu Gly Asp Ile Lys Ser Arg Gln Leu Leu
                380                 385                 390

Ser Asp Ala Val Tyr Leu Phe Ser Cys Gly Gly Asn Asp Tyr Gln
                395                 400                 405

Ser Pro Tyr Tyr Pro Tyr Thr Gln Glu Gln Tyr Val Asp Ile Val
                410                 415                 420

Ile Gly Asn Met Thr Asn Val Ile Lys Gly Ile Tyr Glu Lys Gly
                425                 430                 435

Gly Arg Lys Phe Gly Val Val Asn Val Pro Leu Ile Gly Cys Trp
                440                 445                 450

Pro Gly Met Arg Ala Lys Gln Pro Gly Asn Ala Cys Asn Thr Glu
                455                 460                 465

Val Asp Glu Leu Thr Arg Leu His Asn Gln Ala Phe Ala Lys Thr
                470                 475                 480

Leu Glu His Leu Glu Lys Gln Leu Glu Gly Phe Val Tyr Ala Lys
                485                 490                 495

Phe Asp Leu Ser Thr Ala Ile Leu Asn Arg Met Lys Asn Pro Ser
                500                 505                 510

Lys Tyr Gly Phe Lys Glu Gly Glu Ser Ala Cys Cys Gly Ser Gly
                515                 520                 525

Pro Phe Gly Gly Asn Tyr Asp Cys Gly Arg Ile Lys Glu Phe Gly
                530                 535                 540

Leu Cys Asp Asn Ala Thr Glu Tyr Phe Phe Asp Pro Phe His
                545                 550                 555

Pro Asn Glu Leu Ala Ser Arg Gln Phe Ala Glu Met Phe Trp Asp
                560                 565                 570

Gly Asp Ser Met Val Thr Gln Pro Tyr Asn Leu Lys Ala Leu Phe
                575                 580                 585

Glu Gly Lys Pro Ser Thr Lys Tyr Leu Pro Asn Asp Glu Leu
                590                 595

<210> SEQ ID NO 5
<211> LENGTH: 365
<212> TYPE: PRT
<213> ORGANISM: Pyrethrum Cinerariifolium

<400> SEQUENCE: 5

Met Ala Val Ala Ser Arg Lys Leu Gly Ala Leu Val Leu Val Ala
1               5                   10                  15

Val Leu Cys Leu Ser Leu Pro Thr Gly Cys Leu Ser Ser Gln Gln
                20                  25                  30

Ala Ala Ala Leu Phe Ile Phe Gly Asp Ser Val Phe Asp Pro Gly
                35                  40                  45

Asn Asn Asn His Ile Asn Thr His Val Asn Phe Lys Ala Asn Phe
                50                  55                  60

Trp Pro Tyr Gly Gln Ser Tyr Phe Ser Ser Pro Thr Gly Arg Phe
                65                  70                  75

Ser Asp Gly Arg Ile Ile Pro Asp Phe Ile Ala Glu Tyr Ala Ser
                80                  85                  90
```

```
Leu Pro Ile Ile Pro Ala Tyr Leu Glu Pro Asn Asn Asp Phe Thr
            95                  100                 105

His Gly Ala Asn Phe Ala Ser Ala Gly Ala Gly Leu Ile Ala
        110                 115                 120

Ser His Ala Gly Leu Ala Val Gly Leu Gln Thr Gln Leu Arg Tyr
            125                 130                 135

Phe Gly Asp Leu Val Asp His Tyr Arg Gln Asn Leu Gly Asp Ile
            140                 145                 150

Lys Ser Arg Gln Leu Leu Ser Asp Ala Val Tyr Leu Phe Ser Cys
            155                 160                 165

Gly Gly Asn Asp Tyr Gln Ser Pro Tyr Tyr Pro Tyr Thr Gln Glu
            170                 175                 180

Gln Tyr Val Asp Ile Val Ile Gly Asn Met Thr Asn Val Ile Lys
            185                 190                 195

Gly Ile Tyr Glu Lys Gly Gly Arg Lys Phe Gly Val Val Asn Val
            200                 205                 210

Pro Leu Ile Gly Cys Trp Pro Gly Met Arg Ala Lys Gln Pro Gly
            215                 220                 225

Asn Ala Cys Asn Thr Glu Val Asp Glu Leu Thr Arg Leu His Asn
            230                 235                 240

Gln Ala Phe Ala Lys Arg Leu Glu His Leu Glu Lys Glu Leu Glu
            245                 250                 255

Gly Phe Val Tyr Ala Lys Phe Asp Leu Ser Thr Ala Ile Leu Asn
            260                 265                 270

Arg Met Lys Asn Pro Ser Lys Tyr Gly Phe Lys Glu Gly Glu Ser
            275                 280                 285

Ala Cys Cys Gly Ser Gly Pro Phe Gly Gly Asn Tyr Asp Cys Gly
            290                 295                 300

Arg Ile Lys Glu Phe Gly Leu Cys Asp Asn Ala Thr Glu Tyr Phe
            305                 310                 315

Phe Phe Asp Pro Phe His Pro Asn Glu Leu Ala Ser Arg Gln Phe
            320                 325                 330

Ala Glu Met Phe Trp Asp Gly Asp Ser Met Val Thr Gln Pro Tyr
            335                 340                 345

Asn Leu Lys Ala Leu Phe Glu Gly Lys Pro Ser Thr Lys Phe Leu
            350                 355                 360

Pro Asn Asp Glu Leu
            365

<210> SEQ ID NO 6
<211> LENGTH: 365
<212> TYPE: PRT
<213> ORGANISM: Pyrethrum Cinerariifolium

<400> SEQUENCE: 6

Met Ala Val Ala Ser Arg Lys Leu Gly Ala Leu Val Leu Val Ala
1               5                   10                  15

Val Leu Cys Leu Ser Leu Pro Thr Gly Cys Leu Ser Ser Gln Gln
            20                  25                  30

Ala Ala Ala Leu Phe Ile Phe Gly Asp Ser Val Phe Asp Pro Gly
            35                  40                  45

Asn Asn Asn His Ile Asn Thr His Val Asn Phe Lys Ala Asn Phe
            50                  55                  60

Trp Pro Tyr Gly Gln Ser Tyr Phe Ser Ser Pro Thr Gly Arg Phe
            65                  70                  75
```

-continued

```
Ser Asp Gly Arg Ile Ile Pro Asp Phe Ile Ala Glu Tyr Ala Ser
            80                  85                  90

Leu Pro Ile Ile Pro Ala Tyr Leu Glu Pro Asn Asn Asp Phe Thr
            95                 100                 105

His Gly Ala Asn Phe Ala Ser Ala Gly Ala Gly Ala Leu Ile Ala
           110                 115                 120

Ser His Ala Gly Leu Ala Val Gly Leu Gln Thr Gln Leu Arg Tyr
           125                 130                 135

Phe Gly Asp Leu Val Asp His Tyr Arg Gln Asn Leu Gly Asp Ile
           140                 145                 150

Lys Ser Arg Gln Leu Leu Ser Asp Ala Val Tyr Leu Phe Ser Cys
           155                 160                 165

Gly Gly Asn Asp Tyr Gln Ser Pro Tyr Tyr Pro Tyr Thr Gln Glu
           170                 175                 180

Gln Tyr Val Asp Ile Val Ile Gly Asn Met Thr Asn Val Ile Lys
           185                 190                 195

Gly Ile Tyr Glu Lys Gly Gly Arg Lys Phe Gly Val Val Asn Val
           200                 205                 210

Pro Leu Ile Gly Cys Trp Pro Gly Met Arg Ala Lys Gln Pro Gly
           215                 220                 225

Asn Thr Cys Asn Thr Glu Val Asp Glu Leu Thr Arg Leu His Asn
           230                 235                 240

Gln Ala Phe Ala Lys Arg Leu Glu Gln Leu Glu Lys Gln Leu Glu
           245                 250                 255

Gly Phe Val Tyr Ala Lys Phe Asp Leu Ser Thr Ala Ile Leu Asn
           260                 265                 270

Arg Met Lys Asn Pro Ser Lys Tyr Gly Phe Lys Glu Gly Glu Ser
           275                 280                 285

Ala Cys Cys Gly Ser Gly Pro Phe Gly Asn Tyr Asp Cys Gly
           290                 295                 300

Arg Ile Lys Glu Phe Gly Leu Cys Asp Asn Ala Thr Glu Tyr Phe
           305                 310                 315

Phe Phe Asp Pro Phe His Pro Asn Glu Leu Ala Ser Arg Gln Phe
           320                 325                 330

Ala Glu Met Phe Trp Asp Gly Asp Ser Met Val Thr Gln Pro Tyr
           335                 340                 345

Asn Leu Lys Ala Leu Phe Glu Gly Lys Pro Ser Thr Lys Phe Leu
           350                 355                 360

Pro Asn Asp Glu Leu
           365

<210> SEQ ID NO 7
<211> LENGTH: 365
<212> TYPE: PRT
<213> ORGANISM: Pyrethrum Cinerariifolium

<400> SEQUENCE: 7

Met Ala Val Ala Ser Arg Lys Leu Gly Ala Leu Val Leu Val Ala
1               5                  10                  15

Val Leu Cys Leu Ser Leu Pro Thr Gly Cys Leu Ser Ser Gln Gln
            20                  25                  30

Ala Ala Ala Leu Phe Ile Phe Gly Asp Ser Val Phe Asp Pro Gly
            35                  40                  45

Asn Asn Asn His Ile Asn Thr His Val Asn Phe Lys Ala Asn Phe
            50                  55                  60
```

```
Trp Pro Tyr Gly Gln Ser Tyr Phe Ser Ser Pro Thr Gly Arg Phe
             65                  70                  75

Ser Asp Gly Arg Ile Ile Pro Asp Phe Ile Ala Glu Tyr Ala Ser
             80                  85                  90

Leu Pro Ile Ile Pro Ala Tyr Leu Glu Pro Asn Asn Asp Phe Thr
             95                 100                 105

His Gly Ala Asn Phe Ala Ser Ala Gly Ala Gly Ala Leu Ile Ala
            110                 115                 120

Ser His Ala Gly Leu Ala Val Gly Leu Gln Thr Gln Leu Arg Tyr
            125                 130                 135

Phe Gly Asp Leu Val Asp His Tyr Arg Gln Asn Leu Gly Asp Ile
            140                 145                 150

Lys Ser Arg Gln Leu Leu Ser Asp Ala Val Tyr Leu Phe Ser Cys
            155                 160                 165

Gly Gly Asn Asp Tyr Gln Ser Pro Tyr Tyr Pro Tyr Thr Gln Glu
            170                 175                 180

Gln Tyr Val Asp Ile Val Ile Gly Asn Met Thr Asn Val Ile Lys
            185                 190                 195

Gly Ile Tyr Glu Lys Gly Gly Arg Lys Phe Gly Val Val Asn Val
            200                 205                 210

Pro Leu Ile Gly Cys Trp Pro Gly Met Arg Ala Lys Gln Pro Gly
            215                 220                 225

Asn Thr Cys Asn Thr Glu Val Asp Glu Leu Thr Arg Leu His Asn
            230                 235                 240

Gln Ala Phe Ala Lys Arg Leu Glu Gln Leu Lys Gln Leu Glu
            245                 250                 255

Gly Phe Val Tyr Ala Lys Phe Asp Leu Ser Thr Ala Ile Leu Asn
            260                 265                 270

Arg Met Lys Asn Pro Ser Lys Tyr Gly Phe Lys Glu Gly Glu Ser
            275                 280                 285

Ala Cys Cys Gly Ser Gly Pro Phe Gly Asn Tyr Asp Cys Gly
            290                 295                 300

Arg Ile Lys Glu Phe Gly Leu Cys Asp Asn Ala Thr Glu Tyr Phe
            305                 310                 315

Phe Phe Asp Pro Phe His Pro Asn Glu Leu Ala Ser Arg Gln Phe
            320                 325                 330

Ala Glu Met Phe Trp Asp Gly Asp Ser Met Val Thr Gln Pro Tyr
            335                 340                 345

Asn Leu Lys Ala Leu Phe Glu Gly Lys Pro Ser Thr Lys Tyr Leu
            350                 355                 360

Pro Asn Asp Glu Leu
            365

<210> SEQ ID NO 8
<211> LENGTH: 365
<212> TYPE: PRT
<213> ORGANISM: Pyrethrum Cinerariifolium

<400> SEQUENCE: 8

Met Ala Val Ala Ser Arg Lys Leu Gly Ala Leu Val Leu Val Ala
1               5                  10                  15

Val Leu Cys Leu Ser Leu Pro Thr Gly Cys Leu Ser Ser Gln Gln
             20                  25                  30

Ala Ala Ala Leu Phe Ile Phe Gly Asp Ser Val Phe Asp Pro Gly
             35                  40                  45
```

```
Asn Asn Asn His Ile Asn Thr His Val Asn Phe Lys Ala Asn Phe
             50                  55                  60

Trp Pro Tyr Gly Gln Ser Tyr Phe Ser Ser Pro Thr Gly Arg Phe
             65                  70                  75

Ser Asp Gly Arg Ile Ile Pro Asp Phe Ile Ala Glu Tyr Ala Ser
             80                  85                  90

Leu Pro Ile Ile Pro Ala Tyr Leu Glu Pro Asn Asn Tyr Phe Thr
             95                 100                 105

His Gly Ala Asn Phe Ala Ser Ala Gly Ala Gly Ala Leu Ile Ala
            110                 115                 120

Ser His Ala Gly Leu Ala Val Gly Leu Gln Thr Gln Leu Arg Tyr
            125                 130                 135

Phe Gly Asp Leu Val Asp His Tyr Arg Gln Asn Leu Gly Asp Ile
            140                 145                 150

Lys Ser Arg Gln Leu Leu Ser Asp Ala Val Tyr Leu Phe Ser Cys
            155                 160                 165

Gly Gly Asn Asp Tyr Gln Ser Pro Tyr Tyr Pro Tyr Thr Gln Glu
            170                 175                 180

Gln Tyr Val Asp Ile Val Ile Gly Asn Met Thr Asn Val Ile Lys
            185                 190                 195

Gly Ile Tyr Glu Lys Gly Gly Arg Lys Phe Gly Val Val Asn Val
            200                 205                 210

Pro Leu Ile Gly Cys Trp Pro Gly Met Arg Ala Lys Gln Pro Gly
            215                 220                 225

Asn Thr Cys Asn Thr Glu Val Asp Glu Leu Thr Arg Leu His Asn
            230                 235                 240

Gln Ala Phe Ala Lys Arg Leu Glu Gln Leu Glu Lys Gln Leu Glu
            245                 250                 255

Gly Phe Val Tyr Ala Lys Phe Asp Leu Ser Thr Ala Ile Leu Asn
            260                 265                 270

Arg Met Lys Asn Pro Ser Lys Tyr Gly Phe Lys Glu Gly Glu Ser
            275                 280                 285

Ala Cys Cys Gly Ser Gly Pro Phe Gly Gly Asn Tyr Asp Cys Gly
            290                 295                 300

Arg Ile Lys Glu Phe Gly Leu Cys Asp Asn Ala Thr Glu Tyr Phe
            305                 310                 315

Phe Phe Asp Pro Phe His Pro Asn Glu Leu Ala Ser Arg Gln Phe
            320                 325                 330

Ala Glu Met Phe Trp Asp Gly Asp Ser Met Val Thr Gln Pro Tyr
            335                 340                 345

Asn Leu Lys Ala Leu Phe Glu Gly Lys Pro Ser Thr Lys Tyr Leu
            350                 355                 360

Pro Asn Asp Glu Leu
            365

<210> SEQ ID NO 9
<211> LENGTH: 1098
<212> TYPE: DNA
<213> ORGANISM: Pyrethrum Cinerariifolium
<220> FEATURE:
<221> NAME/KEY: misc_feature
<222> LOCATION: (21)..(21)
<223> OTHER INFORMATION: w = a or t/u
```

```
<400> SEQUENCE: 9
atggctgttg caagcagcaa wcggggtgct cttgttttgg ttgctgtttt gtgtctttca      60
ctacctacag gttgcctgag ttctcaacaa gctgctgcac tatttatatt tggtgattcg     120
gttttcgatc ctggtaacaa taaccacatc aacacccatg ttaattttaa agcgaacttt     180
tggccatatg gtcaatccta cttcagttca ccaactggta gattctctga tggccgtatc     240
atccctgatt tcattgctga gtatgcaagt ctgcctatca ttcctgcgta tctcgagcca     300
aacaatgatt ttacgcatgg agcmaacttt gcgtcagcag gagccggtgc cttgattgcc     360
tcccatgctg gacttgcagt tggccttcaa acacaactac attactttgg cgatttagta     420
gaccattatc ggcagaattt aggtgatatt aaatctaggc agctactatc cgatgctgtc     480
tacttgttta gctgtggagg taacgactac caaagccctt actatccata tactcaagag     540
caatacgtgg acattgtgat tggaaacatg actaacgtca tcaagggaat atacgaaaaa     600
ggtggaagaa aatttggggt tgtgaatgtc ccgcttatag gctgttggcc gggaatgcga     660
gcaaaacaac ctggaaatgc ttgcaacaca gaggtcgatg aacttactag actacacaat     720
caagcatttg caaaaacact agaacatttg gagaaacagt tggaaggctt tgtgtatgct     780
aaattcgatc tttcaactgc cattctcaat agaatgaaga ccccctcaaa atatggtttt     840
aaggaaggcg agagcgcatg ttgcggtagt ggtccttttg gagggaatta tgattgtggc     900
agaataaaag agtttggact atgtgataat gcaactgagt attttttctt tgacccttt      960 catcctaatg aattggcgag tcgccaattt gcagagatgt tttgggatgg ggattccatg    1020
gtcacacagc cttacaattt gaaagcactc tttgaaggga agccatcaac aaaatatctc    1080
ccaaatgatg agctctaa                                                  1098

<210> SEQ ID NO 10
<211> LENGTH: 1098
<212> TYPE: DNA
<213> ORGANISM: Pyrethrum Cinerariifolium
<220> FEATURE:
<221> NAME/KEY: misc_feature
<222> LOCATION: (324)..(324)
<223> OTHER INFORMATION: m = a or c

<400> SEQUENCE: 10
atggctgttg caagcagaaa actgggtgct cttgttttgg ttgctgtttt gtgtctttca      60
ctacctacag gttgccttag ttctcaacaa gctgctgcac tatttatatt tggtgattcg     120
gttttcgatc ctggtaacaa taaccacatc aacacccatg ttaattttaa agcgaacttt     180
tggccatatg gtcaatccta cttcagttca ccaactggta gattctctga tggccgtatc     240
atccctgatt tcattgctga gtatgcaagt ctgcctatca ttcctgcgta tctcgagcca     300
aacaatgatt ttacgcatgg agcmaacttt gcgtcagcag gagctggtgc cttgattgcc     360
tcccatgctg gacttgcagt tggccttcaa acacaactac gttactttgg cgatttagta     420
gaccattatc ggcagaattt aggtgatatt aaatctaggc agctactatc cgatgctgtc     480
tacttgttta gctgtggagg taacgactac caaagccctt actatccata tactcaagag     540
caatacgtcg acattgtgat tggaaacatg actaacgtca tcaarggaat atacgaaaaa     600
ggtggaagaa aatttggggt tgtgaatgtc ccgcttatag gctgttggcc gggaatgcga     660
gcaaaacaac ctggaaatgc ttgcaacaca gaggtcgatg aacttactag actacacaat     720
caagcatttg caaaaagact agaacatttg gagaaagagt tggaaggctt tgtgtatgct     780
aaattcgatc tttcaactgc cattctcaat agaatgaaga ccccctcaaa atatggtttt     840
```

```
aaggaaggcg agagcgcatg ttgcggtagt ggtccttttg gagggaatta tgattgtggc    900
agaataaaag agtttggact atgtgataat gcaactgagt attttttctt tgacccttt     960
catcctaatg aattggcgag tcgccaattt gcagagatgt tttgggatgg ggattccatg   1020
gtcacacagc cttacaattt gaaagcactc tttgaaggga agccatcaac aaaatttctc   1080
ccaaatgatg agctctaa                                                 1098
```

<210> SEQ ID NO 11
<211> LENGTH: 1098
<212> TYPE: DNA
<213> ORGANISM: Pyrethrum Cinerariifolium

<400> SEQUENCE: 11

```
atggctgttg caagcagaaa actgggtgct cttgttttgg ttgctgtttt gtgtctttca     60
ctacctacag gttgccttag ttctcaacaa gctgctgcac tatttatatt tggtgattcg    120
gttttcgatc ctggtaacaa taaccacatc aacacccatg ttaattttaa agcgaacttt    180
tggccatatg gtcaatccta cttcagttca ccaactggta gattctctga tggccgtatc    240
atccctgatt tcattgctga gtatgcaagt ctgcctatca ttcctgcgta tctcgagcca    300
aacaatgatt ttacgcatgg agccaacttt gcgtcagcag gagctggtgc cttgattgcc    360
tcccatgctg gacttgcagt tggccttcaa acacaactac gttactttgg cgatttagta    420
gaccattatc ggcagaattt aggtgatatt aaatctaggc agctactatc cgatgctgtc    480
tacttgttta gctgtggagg taacgactac aaagcccctt actatccata tactcaagag    540
caatacgtgg acattgtgat ggaaacatg  actaacgtca tcaagggaat atacgaaaaa    600
ggtggaagaa atttggtgt  tgtgaatgtc ccgcttatag gctgttggcc gggaatgcga    660
gcaaaacaac ctggaaatac ttgcaacaca gaggtcgatg aacttactag actacacaat    720
caagcatttg caaaaagact agaacaattg gagaaacagt tggaaggctt tgtgtatgct    780
aaattcgatc tttcaactgc cattctcaat agaatgaaga ccccctcaaa atatggtttt    840
aaggaaggcg agagcgcatg ttgcggtagt ggtccttttg gagggaatta tgattgtggc    900
agaataaaag agtttggact atgtgataat gcaactgagt attttttctt tgacccttt     960
catcctaatg aattggcgag tcgccaattt gcagagatgt tttgggatgg ggattccatg   1020
gtcacacagc cttacaattt gaaagcactc tttgaaggga agccatcaac aaaatttctc   1080
ccaaatgatg agctctaa                                                 1098
```

<210> SEQ ID NO 12
<211> LENGTH: 1098
<212> TYPE: DNA
<213> ORGANISM: Pyrethrum Cinerariifolium

<400> SEQUENCE: 12

```
atggctgttg caagcagaaa actgggtgct cttgttttgg ttgctgtttt gtgtctttca     60
ctacctacag gttgccttag ttctcaacaa gctgctgcac tatttatatt tggtgattcg    120
gttttcgatc ctggtaacaa taaccacatc aacacccatg ttaattttaa agcgaacttt    180
tggccatatg gtcaatccta cttcagttca ccaactggta gattctctga tggccgtatc    240
atccctgatt tcattgctga gtatgcaagt ctgcctatca ttcctgcgta tctcgagcca    300
aacaatgatt ttacgcatgg agcmaacttt gcgtcagcag gagctggtgc cttgattgcc    360
tcccatgctg gacttgcagt tggccttcaa acacaactac gttactttgg cgatttagta    420
gaccattatc ggcagaattt aggtgatatt aaatctaggc agctactatc cgatgctgtc    480
```

```
tacttgttta gctgtggagg taacgactac caaagccctt actatccata tactcaagag    540
caatacgtsg acattgtgat tggaaacatg actaacgtca tcaagggaat atacgaaaaa    600
ggtggaagaa atttggtgt tgtgaatgtc ccgcttatag gctgttggcc gggaatgcga     660
gcaaaacaac ctggaaatac ttgcaacaca gaggtcgatg aacttactag actacacaat    720
caagcatttg caaaaagact agaacaattg gagaaacagt tggaaggctt tgtgtatgct    780
aaattcgatc tttcaactgc cattctcaat agaatgaaga cccctcaaa atatggtttt     840 aaggaaggcg agagcgcatg ttgcggtagt ggtccttttg gagggaatta tgattgtggc    900
agaataaaag agtttggact atgtgataat gcaactgagt attttttctt tgacccttt     960 catcctaatg aattggcgag tcgccaattt gcagagatgt tttgggatgg ggattccatg    1020
gtcacacagc cttacaattt gaaagcactc tttgaaggga agccatcaac aaaatatctc    1080
ccaaatgatg agctctaa                                                  1098

<210> SEQ ID NO 13
<211> LENGTH: 1098
<212> TYPE: DNA
<213> ORGANISM: Pyrethrum Cinerariifolium

<400> SEQUENCE: 13
atggctgttg caagcagaaa actgggtgct cttgttttgg ttgctgtttt gtgtctttca     60
ctacctacag gttgccttag ttctcaacaa gctgctgcac tatttatatt tggtgattcg    120
gttttcgatc ctggtaacaa taaccacatc aacacccatg ttaattttaa agcgaacttt    180
tggccatatg gtcaatccta cttcagttca ccaactggta gattctctga tggccgtatc    240
atccctgatt tcattgctga gtatgcaagt ctgcctatca ttcctgcgta tctcgagcca    300
aacaattatt ttacgcatgg agccaacttt gcgtcagcag gagctggtgc cttgattgcc    360
tcccatgctg gacttgcagt tggccttcaa acacaactac gttactttgg cgatttagta    420
gaccattatc ggcagaattt aggtgatatt aaatctaggc agctactatc cgatgctgtc    480
tacttgttta gctgtggagg taacgactac caaagccctt actatccata tactcaagag    540
caatacgtgg acattgtgat tggaaacatg actaacgtca tcaagggaat atacgaaaaa    600
ggtggaagaa atttggtgt tgtgaatgtc ccgcttatag gctgttggcc gggaatgcga     660
gcaaaacaac ctggaaatac ttgcaacaca gaggtcgatg aacttactag actacacaat    720
caagcatttg caaaaagact agaacaattg gagaaacagt tggaaggctt tgtgtatgct    780
aaattcgatc tttcaactgc cattctcaat agaatgaaga cccctcaaa atatggtttt     840 aaggaaggcg agagcgcatg ttgcggtagt ggtccttttg gagggaatta tgattgtggc    900
agaataaaag agtttggact atgtgataat gcaactgagt attttttctt tgacccttt     960 catcctaatg aattggcgag tcgccaattt gcagagatgt tttgggatgg ggattccatg    1020
gtcacacagc cttacaattt gaaagcactc tttgaaggga agccatcaac aaaatatctc    1080
ccaaatgatg agctctaa                                                  1098

<210> SEQ ID NO 14
<211> LENGTH: 33
<212> TYPE: PRT
<213> ORGANISM: Pyrethrum Cinerariifolium
```

```
<400> SEQUENCE: 14

Ser Gln Gln Ala Ala Ala Leu Phe Ile Phe Gly Asp Ser Val Phe
1               5                   10                  15

Asp Pro Gly Asn Asn Asn His Ile Asn Thr His Val Asn Phe Lys
                20                  25                  30

Ala Asn Phe

<210> SEQ ID NO 15
<211> LENGTH: 7
<212> TYPE: PRT
<213> ORGANISM: Pyrethrum Cinerariifolium

<400> SEQUENCE: 15

Gln Asn Leu Gly Asp Ile Lys
1               5

<210> SEQ ID NO 16
<211> LENGTH: 9
<212> TYPE: PRT
<213> ORGANISM: Pyrethrum Cinerariifolium

<400> SEQUENCE: 16

Gln Leu Glu Gly Phe Val Tyr Ala Lys
1               5
```